(12) United States Patent
Tsuji et al.

(10) Patent No.: US 6,218,161 B1
(45) Date of Patent: Apr. 17, 2001

(54) SUGAR-CHAIN SYNTHETASE AND PROCESS FOR PRODUCING THE SAME

(75) Inventors: Shuichi Tsuji; Nobuyuki Kurosawa; Toshiro Hamamoto; Young-Choon Lee; Takashi Nakaoka; Naoya Kojima, all of Saitama (JP)

(73) Assignee: The Institute of Physical and Chemical Research, Saitama (JP)

( * ) Notice: Subject to any disclaimer, the term of this patent is extended or adjusted under 35 U.S.C. 154(b) by 0 days.

(21) Appl. No.: 09/143,438

(22) Filed: Aug. 28, 1998

Related U.S. Application Data

(62) Division of application No. 08/666,367, filed as application No. PCT/JP94/02182 on Dec. 22, 1994, now Pat. No. 5,854,042.

(30) Foreign Application Priority Data

Dec. 24, 1993 (JP) .................................... 5-348260
Mar. 28, 1994 (JP) .................................... 6-57369
Apr. 28, 1994 (JP) .................................... 6-91507

(51) Int. Cl.$^7$ .................................................. C12N 15/54
(52) U.S. Cl. .................. 435/193; 435/252.3; 435/320.1; 536/23.2
(58) Field of Search .............................. 435/193, 320.1, 435/252.3; 536/23.2

(56) References Cited

FOREIGN PATENT DOCUMENTS

90/12090  10/1990  (WO) .

OTHER PUBLICATIONS

J. Sadler et al., "Purification to Homogeneity of a β–Galactoside α2→3 Sialyltransferase and Partial Purification of an α–N–Acetylgalactosaminide α2→6 Sialyltransferase from Porcine Submaxillary Glands", The Journal of Biological Chemistry, vol. 254, No. 11, Jun. 10, 1979, pp. 4434–4443.

J. Sadler et al., "Purification to Homogeneity and Enzymatic Characterization of an α–N–Acetylgalactosaminide α2→6 Sialyltransferase from Porcine Submaxillary Glands", The Journal of Biological Chemistry, vol. 254, No. 13, Jul. 10, 1979, pp. 5934–5941.

Blumenfeld, O.O., et al. (1992), Blood 80(9), pp. 2388–2395.

Gross, H.J., et al. (1989), Biochemistry 28, pp. 7386–7392.

Gross, H.J., et al. (1988), Eur. J. Biochem. 177, pp. 583–589.

Higa, H.H., et al. (1985), J. Biol. Chem. 260(15), pp. 8839–8849.

Kurosawa, N., et al. (1994), J. Biol. Chem. 263(2), pp. 1402–1409.

Kurosawa, N., et al. (1994), J. Biol. Chem., 269(29), pp. 19048–19053.

J. Weinstein et al. "Primary Structure of β–Galactoside α2,6–Sialyltransferase", The Journal of Biological Chemistry, vol. 262, No. 36, pp. 17735–17743, Dec. 25, 1987.

D. Wen et al. "Primary Structure of Galβ1,3(4)GlcNAc α2,3–Sialyltransferase Determined by Mass Spectrometry Sequence Analysis and Molecular Cloning", The Journal of Biological Chemistry, vol. 267, No. 29, pp. 21011–21019, Oct. 15, 1992.

W. Gillespie et al. "Cloning and Expression of the Galβ1, 3GalNAc α2,3–Sialyltransferase", The Journal of Biological Chemistry, vol. 267, No. 29, pp. 21004–21010, Oct. 15, 1992.

S. Hakomori, "Glycosphingolipids in Cellular Interaction, Differentiation, and Oncogenesis[1]", Ann. Rev. Biochem., vol. 50, pp. 733–764, 1981.

Toshiro Hamamoto et al., "Two Step Single Primer Mediated Polymerase Chain Reaction.[1] Application to Cloning of Putative Mouse, β–Galactoside α2,6–Sialyltransferase cDNA", Bioorganic & Medicinal Chemistry, vol. 1, No. 2, pp. 141–145, 1993.

*Primary Examiner*—Charles L. Patterson, Jr.
(74) *Attorney, Agent, or Firm*—Wenderoth, Lind & Ponack, L.L.P.

(57) ABSTRACT

Novel GalNAcα2,6-sialyltransferases P-B1 and P-B3; GalNAcα2,6-sialyltransferase genes encoding the above GalNAcα2,6-sialyltransferases P-B1 and P-B3; and an extracellularly releasable protein catalyzing GalNAcα2,6-sialic acid transfer which comprises a polypeptide portion as being an active domain of the GalNAcα2,6-sialyltransferase P-B1 or P-B3 together with a signal peptide are provided. Also provided is a process for preparing a sialyltransferases which enables efficient recovery of a sialyltransferase expressed in a large quantity in microorganisms.

31 Claims, 5 Drawing Sheets

FIG. 4A

```
P-B3  : MG--------SPRWKRFCFLLAAFTSSLLLYGHYYATVDVRSGPRVVTSL
         ||                                   ||
P-B1  : MGFLIRRLPKDSRIFRWLLILTVFSFIITSFSALFGMEKSIFRQLKIYQSIA

P-B3  : KQPTPCPRSVAATAKADPTFGELFQFDIPVLM----------------
         |
P-B1  : EQKKTVKPVAKVEEAKEKVTVKPFPEVMGITNTTASTASVVERTKEKTTARP

P-B3  : ------------------------------------------------

P-B1  : AEEPPASVKAIRPVTQAATVTEKKKLRAADFKTEPQWDFDDEYILDSSSPVS

P-B3  : WDQHFNPETWDRLKARRVPYGWQGLSQAAVGSTLRLFDRHLFPGGCIRCAVV
         |    |       |     |      |   ||  |    ||  | |||
P-B1  : GFMELNYSLVEEVMSRLPPNPHQQLLANSSSNVSTLNTSSNTRLC SCAVV

P-B3  : TMKNSLIAYEAYGFTRTPQGKDLKYIFIPSDARDYIMLRSAIQGSPVPEG-L
         |   |||     |   | ||  |   |
P-B1  : SLVSSLQNLGHKGFKKIPQGKHIRYIHFLEAVRDYEWLKALLLDKDIRKGFL

P-B3  : YMPSTGALMLLTALHTCDQVSAYGFITANYEQFSDHYYEPEKKPLVFEYANHD
         || |||| ||||||  | ||||||||
P-B1  : YRPTTGALLLLTALHLCDRVSAYGYITEGHQKYSDHYYDKEWKRLVFYVNHD
```

```
4A| LQPELLFLVRPDTPHPDNSHHKELRGTVKSREFFSQPSSELEKPKPSG    - 91
                |
   HMLQVDTQDQQGSNYSANGRISKVGLERDIAWLELNTAVSTPSGEGKE   -100
                                                     -123

VPGVGEADGKRTTIALPSMKEDKEKATVKPSFGMKVAHANSTSKDKPK   -200
                                                     -123

TCSESVRAKAAKSDWLRDLFLPNITLFIDKSYFNVSEWDRLEHFAPPY   -300

GNGGILNGSRQGRAIDAHDLVFRLNGAITKGFEEDVGSKVSFYGFTVN   -223
   ||||||||||  ||  |  |||||  | |  | | ||   ||||||
   GNGGILNNSGMGQEIDSHDYVFRVSGAVIKGYEKDVGTKISFYGFTAY   -400

DKGDEPQKYFGLEASAEKFKLL-HPDFLHYLTTRFLRSELLDMQYGHL   -321
      | |||   |  ||  |    |||| ||  ||||  |    |
   NYYGRRPRERFDEDFTMNKYLVAHPDFLRYLKNRFLKSKNLQKPYWRL   -500

MLLEAELWRSLHRAGIMELYQR                             -404
   |  |     |||| ||  |||
4A| FNLEKQVWKRLHDENIMKLYQRS                            -566
```

SUGAR-CHAIN SYNTHETASE AND PROCESS FOR PRODUCING THE SAME

This application is a divisional application of Ser. No. 08/666,367, filed Aug. 19, 1996, now U.S. Pat. No. 5,854, 042, which is the national stage of PCT/JP94/02182, filed Dec. 22, 1994.

BACKGROUND OF THE INVENTION

1. Field of the Invention

The present invention relates to a sugar-chain synthetase and a DNA encoding the enzyme. More specifically, the present invention relates to an N-acetylgalactosamineα2,6-sialyltransferase (GalNAc α2,6-sialyltransferase) and a DNA encoding the enzyme. The enzyme is useful as medicaments having inhibitory activities against tumor metastases and viral infection, and as agents for introducing a sialic acid moieties into drugs to increase their biological activity.

The present invention further relates to a process for producing the sugar-chain synthetase. More specifically, the present invention relates to a process for expressing sialyltransferases in microorganisms to obtain the sialyltransferases in large quantities.

2. Description of Related Art

Sialic acids play an important role in a variety of biological processes, like cell-cell communication, cell-substrate interaction, adhesion. It has been known that various kinds of distinguishable cell surface sialic acids exist which change in a regulated manner during development, differentiation, and oncogenic transformation.

Sialic acids occur at the terminal positions of the carbohydrate groups of glycoproteins and glycolipids, and they are enzymatically introduced from CMP-Sia to these positions in a post translational process. For example, three linkage patterns, Siaα2,6Gal, Siaα2,3Gal and Siaα2,6GalNAc are commonly found in glycoproteins (Hakomori, S., Ann. Rev. Biochem., 50, pp.733–764, 1981), and two, Siaα2,3Gal and Siaα2,8Sia, occur frequently in gangliosides (Fishman, P., and Brady, R. O., Science, 194, pp.906–915, 1976).

The enzymes responsible for such enzymatic introduction of sialic acid (sialic acid transfer) as mentioned above are glycosyltransferases called sialyltransferases. It has been known that at least 12 different sialyltransferases are required to synthesize all known sialyloligosaccharide structures (Broquet, P. et al., Int. J. Biochem., 23, 385–389, 1991; and Weinstein, J. et al., J. Biol. Chem., 262, 17735–17743, 1987). Among these enzymes, five sialyltransferases have been purified so far, and it has been known that they exhibit strict specificity for acceptor substrate (Sadler, J. et al., J. Bio. Chem., 254, pp.4434–4443, 1979; Weinstein, J. et al., J. Biol. Chem., 257, pp.13835–13844, 1982; Rearick, J. et al., J. Biol. Chem., 254, pp.4444–4451, 1979; and Joqiasse, D. H. et al., J. Biol. Chem., 260, 4941–4951, 1985).

As for cDNAs encoding the aforementioned sialyltransferases, cDNAs encoding Galβ1,4GlcNAcα2,6-sialyltransferase (Galβ4GlcNAc-α6ST) have been cloned from various organs including liver (Weinstein, J. et al., J. Biol. Chem., 262, pp.17735–17743, 1987; Grundmann U. et al., Nucleic Acids Res. 18, 667, 1990; Bast, B. et al., J. Cell. Biol., 116, pp.423–435, 1992; and Yamamoto, T. et al., Bioorg. and Medic. Chem., 1, pp.141–145, 1993). Furthermore, cDNAs encoding Galβ1,3GalNAcα2,3-sialyltransferase (Galβ3GalNAc-α3ST) (Gillespie, W. et al., J. Biol. Chem., 267, pp.21004–21010, 1992: Japanese Patent Unexamined Publication No. 5-504678/1993; and Lee, Y. et al., Eur. J. Biochem, 216, 377–385, 1993); Galβ1,3(4) GlcNAcα2,3-sialyltransferase (Galβ3(4)GlcNAc-α3ST) (Wen, D. X et al., J. Biol. Chem., 267, 21011–21019,1992; and Kitagawa, H. et al., Biochem. Biophys. Res. Commun. 194, 375); and Galβ1,3GalNAc/Galβ1,4GlcNAcα2,3-sialyltransferase (Sasaki, K. et al., J. Biol. Chem., 268, 22782–22787, 1993) have also been cloned.

With respect to GalNAcα2,6-sialyltransferase, the isolation of this enzyme has been reported (Hakomori, S., Ann. Rev. Biochem., 50, 733–764, 1981). However, the enzyme has not been purified so as to be characterized as a single identifiable substance, and accordingly, the enzyme has not been practically used because of insufficient reaction specificity, stability, and quantitative availability. Furthermore, a cDNA sequence encoding GalNAcα2,6-sialyltransferase (EC 2.4.99.3; GalNAc-α6ST) has not yet been cloned.

Each of the aforementioned sialyltransferases whose structures having been revealed has a hydrophobic segment located at the $NH_2$-terminal region, and is a type II transmembrane protein immobilized to cell membrane by the hydrophobic segment. From this reason, a problem arises that expressed enzymes are immobilized to cell membranes and are not capable of being extracellularly released, where expressions are carried out using vectors containing sialyltransferase genes that are transfected into mammalian cells. Furthermore, another problem may arise, when the expression is performed using mammalian cells, that enzyme expressions may be reduced as endoplasmic enzyme concentrations exceed certain levels.

In order to solve the above problems, an extracellularly releasable fused protein may be prepared which comprises an active domain of a sialyltransferase and a signal peptide region. This method is characterized in that a sialyltransferase can be readily recovered from a cell cultivation mixture, because the method involves the step of extracellular release of the fused protein which retains sialyl transfer activity and function as a sialyltransferase. However, where the expression of a sialyltransferase is performed using a mammalian cell, a transfected cell may be unstable or troublesome cultivation procedures are required. In addition, in order to obtain a large quantity of expressed sialyltransferase, a mass cell culture is essential for a long period of time, which may cause disadvantageous from viewpoints of cost and manufactural installations.

Processes are well known to those skilled in the art to obtain cloned cDNA sequence encoding an enzyme expressed in mammalian cells and prepare a recombinant vector containing a gene encoding the enzyme, per se, or in a soluble form, and to transform microorganisms with the vector. A desired enzyme can be produced, in a large quantity, by culturing the transformant obtained by the aforementioned method to allow the microorganism to express the enzyme, per se, or in a soluble form that has the desired activity.

This process comprises, for example, a step of culturing a transformed microorganism and extracting an expressed enzyme by lysis of the microorganisms using lysozyme or the like. However, a large amount of insoluble or soluble proteins is expressed in the microorganisms in a short period of time, and such proteins may aggregate inside the microorganisms to form proteinic aggregates or precipitates. Accordingly, it is necessary to extract the protein from such aggregates or precipitates.

To extract the desired protein from the aforementioned aggregates or precipitates, generally employed methods are those using urea, guanidine hydrochloride and the like. In this approach, the expressed protein is generally subjected to denaturation using, for example, urea for solubilization (by an exposure of the hydrophobic region), and then to renaturation treatment. The renaturation may be achieved by removing the urea through dialysis. However, for the removal of urea, a problem is that optimal conditions including pH, salt concentration, and temperature must be chosen that are strictly specific to each of the enzymes, and this optimization of conditions is extremely time-consuming. If inappropriate conditions are applied, recovered enzyme may retain almost no activity, and therefore, the selection of the conditions for the renaturation is particularly important.

Accordingly, one object of the present invention is to provide purified GalNAcα2,6-sialyltransferase. Another object of the present invention is to provide a DNA sequence encoding GalNAcα2,6-sialyltransferase and an amino acid sequence of the enzyme by cloning a cDNA sequence that encodes GalNAcα2,6-sialyltransferase. Further objects of the present invention are to provide an extracellularly releasable protein comprising an active domain of the GalNAcα2, 6-sialyltransferase and to provide a process for a mass expression of said protein in microorganisms. It is also an object of the invention to provide a process for extraction of an expressed sialyltransferase from aggregate thereof in microorganisms and a process of efficient renaturation of the extract.

SUMMARY OF THE INVENTION

The present inventors conducted various studies to achieve the foregoing objects, and as a result, they succeeded in cloning the cDNA encoding GalNAcα2,6-sialyltransferase from chick embryo. The present invention was achieved on the basis of these findings. The present invention thus provides GalNAcα2,6-sialyltransferase P-B1 characterized by the amino acid sequence disclosed as SEQ ID NO.5 in the sequence listings. The present invention also provides GalNAcα2,6-sialyltransferase genes encoding the aforementioned amino acid sequence of GalNAcα2,6-sialyltransferase P-B1, and as an embodiment thereof, a GalNAcα2,6-sialyltransferase gene characterized by the nucleotide sequence from nucleotide No.1 to 1698 disclosed as SEQ ID NO.1 in the sequence listings. Also provided are recombinant vectors comprising the above GalNAcα2,6-sialyltransferase gene and plasmid λ CEB-3034 as an embodiment thereof, transformants which are transformed with the above recombinant vector, and the active domain of GalNAcα2,6-sialyltransferase characterized by the amino acids of No. 233 through 566 of the amino acid sequence disclosed as SEQ ID NO.5 in the sequence listings.

The GalNAcα2,6-sialyltransferase P-B1 has activity of transferring sialic acid to the 6-position of N-acetylgalactosamine directly bound to a protein regardless of the presence or absence of a substituent on hydroxyl group at the 3-position. The structure of NeuAcα2, 6GalNAc-protein is thus readily formed by the enzyme, which terminates further extension of the resulting sugar chain. Therefore, where a longer sugar chain is desired, a sugar chain synthetic scheme should be designed so that this enzyme can be employed after complete extension of a sugar chain. For this reason, a sialyltransferase is highly useful which fails to transfer sialic acid to an N-acetylgalactosamine that has unsubstituted 3-hydroxyl group and bonded to a protein via an α-glycoside linkage, but can transfer sialic acid to the 6-position of an N-acetylgalactosamine bound to a protein via an α-glycoside linkage, only when the hydroxyl group at 3-position is substituted with a galactose or a sugar chain having a galactose at its reduced terminus.

Therefore, the inventors of the present invention cloned a cDNA from chicken testes that encodes GalNAcα2,6-sialyltransferase having the aforementioned features, and as a result, they achieved the present invention relating to the GalNAcα2,6-sialyltransferase P-B3 characterized by the amino acid sequence disclosed as SEQ ID NO.7 in the sequence listings. The present invention thus provides GalNAcα2,6-sialyltransferase genes encoding the above amino acid sequence of the GalNAcα2,6-sialyltransferase P-B3, and as an embodiment thereof, the GalNAcα2,6-sialyltransferase e gene having the nucleotide sequence of from nucleotide No.1 to 1212 as disclosed as the SEQ ID NO.3 in the sequence listings. The present invention also provides a recombinant vector comprising the above GalNAcα2,6-sialyltransferase gene and plasmid λ CEB3-T20 as an embodiment thereof, and a transformant being transformed with the above recombinant vector.

The inventor of the present invention further conducted studies to provide an extracellularly releasable protein comprising a portion, i.e. active domain, that is derived from the structure of the aforementioned GalNAcα2,6-sialyltransferase and is responsible for its activity. As a result, they succeeded in identifying a partial polypeptide of the above-described GalNAcα2,6-sialyltransferase as being the active domain, and achieved the present invention directed to an extracellularly releasable protein which comprises the polypeptide region together with a signal peptide and catalyzes GalNAcα2,6-sialic acid transfer. As an embodiment thereof, protein SB-690 characterized by the amino acid sequence disclosed as SEQ ID NO.6 in the sequence listings. The present invention also provides genes encoding the above protein, and as an embodiment thereof, a gene having the nucleotide sequence characterized by nucleotide No. 1 to 1065 disclosed as SEQ ID NO.2 of the sequence listings, and a recombinant vector containing the aforementioned gene and plasmid pcDSB-690 as an embodiment thereof. Further provided are a transformant being transformed with the above recombinant vector and a process for preparing the aforementioned protein which comprises the steps of culturing the above transformant and recovering the above protein from the culture.

In addition, the inventors found that a Galβ1,4GalNAcα2, 6-sialyltransferase with a highly restored activity can be prepared by expressing mouse Galβ1,4GalNAcα2,6-sialyltransferase in an insoluble form in *Escherichia coli*, followed by extracting the enzyme with urea and subjecting the enzyme to renaturation under optimal conditions, and thus achieved the present invention. In accordance with the present invention, there is provided a process for producing a sialylransferase which comprises the steps of: (a) expressing a sialyltransferase in a microorganism; (b) extracting the sialyltransferase with about 5 to 9 M urea from proteinic aggregates or precipitates accumulated inside the microorganism and containing the enzyme; (c) diluting the extract obtained by the above step (b) with a renaturation composition to obtain a primary dilution containing about 1 to 4 M urea; (d) diluting the primary dilution obtained by the above step (c) with a renaturation composition to obtain a secondary dilution containing about 0.5 to 2 M urea; and (e) removing urea from the secondary dilution obtained by the above step (d) by dialysis to afford a renatured sialyltransferase.

BRIEF DESCRIPTION OF THE DRAWINGS

FIGS. 4A and 4B show the result of comparison between the primary sequences of GalNAcα2,6-sialyltransferase P-B3 and GalNAcα2,6-sialyltransferase P-B1 according to the present invention. In the figure, amino acids are represented by the one-letter abbreviations.

DESCRIPTION OF THE PREFERRED EMBODIMENTS

Figure 1:
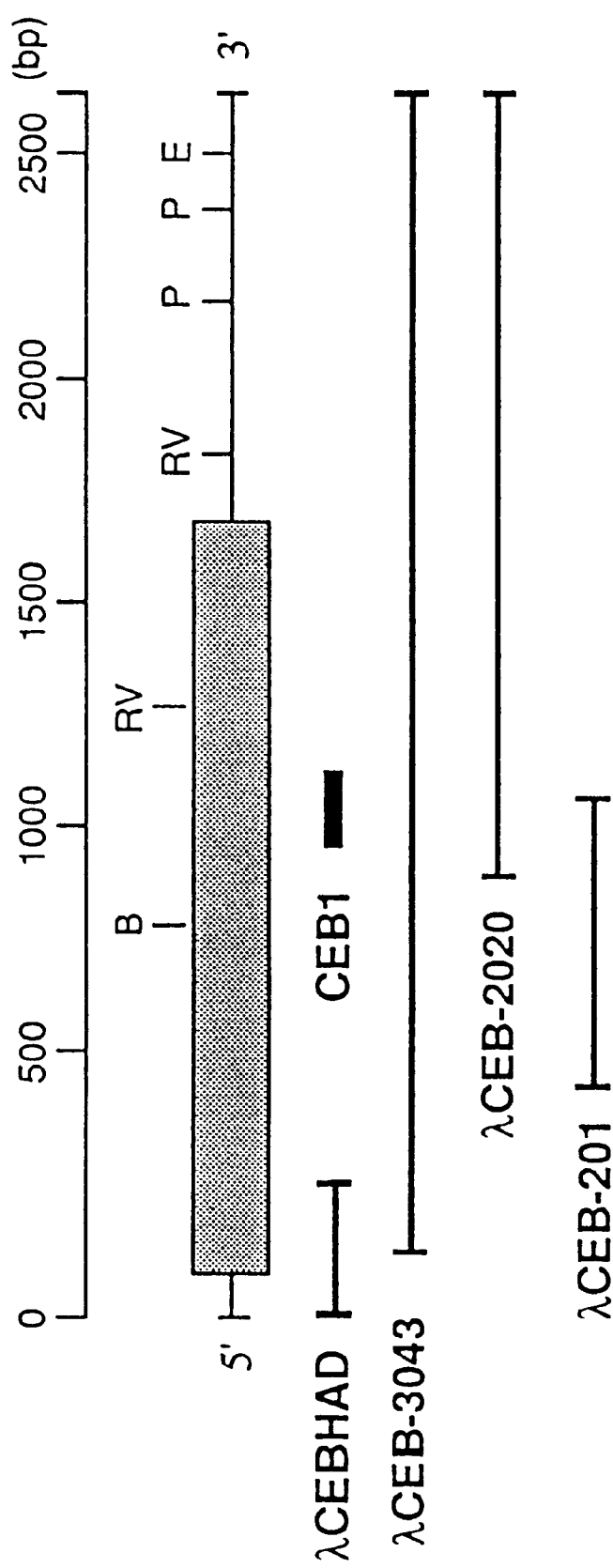
FIG. 1 shows a restriction map of the cDNA clone encoding GalNAcα2,6-sialyltransferase P-B1. In the figure, E represents EcORI; RV: EcoRV; P: PstI; and B: BglII.

As the most preferred embodiments of the present GalNAcα2,6-sialyltransferases, GalNAcα2,6-sialyltransferases P-B1 and P-B3 are provided. The explanations set out below will detail GalNAcα2,6-sialyltransferases P-B1 and P-B3 as examples of the enzyme of the present invention. However, the GalNAcα2,6-sialyltransferases of the present invention are not limited to the GalNAcα2,6-sialyltransferase P-B1 or P-B3. GalNAcα2,6-sialyltransferases comprising the active domain of the GalNAcα2,6-sialyltransferase P-B1 and/or that of P-B3, both were first revealed by the present invention, or alternatively, those comprising one or more active domains of the GaINAcα2,6-sialyltransferase in which the aforementioned acid sequence is partially changed or modified also fall within the scope of the present invention. A preferred example of such active domains as mentioned above is the active domain of the GalNAcα2,6-sialyltransferase characterized by from amino acids No. 233 to 566 of the amino acid sequence disclosed as SEQ ID NO.5 of the sequence listings.

The methods for isolation of the respective cDNAs encoding GalNAcα2,6-sialyltransferase P-B1 and GalNAcα2,6-sialyltransferase P-B3 will be detailed in Examples set out below. However, the methods for isolation of the cDNAs encoding GalNAcα2,6-sialyltransferase P-B1 and GalNAcα2,6-sialyltransferase P-B3 are not limited to those methods. One of ordinarily skilled artisan can readily isolate the desired cDNAs by referring to the methods described in the following examples, or alternatively, by appropriately modifying or altering those methods. In addition, the nucleotide sequences disclosed as SEQ ID Nos.1 through 3 in the sequence listings may be synthetically prepared and used to carry out the present invention.

The DNA sequence encoding GalNAcα2,6-sialyltransferase P-B1 as defined by SEQ ID No.1 in the sequence listings and the DNA sequence encoding GalNAcα2,6-sialyltransferase P-B3 as defined by SEQ ID No.3 are the preferred embodiments of the present invention. However, the DNA sequences encoding GalNAcα2,6-sialyltransferase P-B1 or GalNAcα2,6-sialyltransferase P-B3 of the present invention are not limited to those specified embodiments, and any one of DNA sequences encoding the respective amino acid sequences of GalNAcα2,6-sialyltransferase P-B1 and GalNAcα2,6-sialyltransferase P-B3 revealed by the present invention fall within the scope of the present invention. For example, the DNA sequence encoding the active domain of GalNAcα2,6-sialyltransferase characterized by the amino acids of from No. 233 to 566 of the amino acid sequence as defined by SEQ ID No.5 in the sequence listings is a preferred embodiment of the present invention. In addition, the DNA characterized by the nucleotides sequence of from nucleotide No. 699 to 1698 of the SEQ ID No.1 shown in the sequence listings is a particularly preferred embodiment of the present invention.

The GalNAcα2,6-sialyltransferases of the present invention, including P-B1 and P-B3 for example, may occasionally be retained inside the cells after expression and not released extracellularly. Furthermore, when endoplasmic concentrations of the enzymes exceed certain levels, expressed amounts of the enzymes may possibly be reduced. In order to efficiently utilize the aforementioned GalNAcα2,6-sialic acid transfer activities of GalNAcα2,6-sialyltransferase P-B1 and P-B3, proteins in soluble forms may be prepared in which the activities of these enzymes are retained and can be released extracellularly from cells upon their expressions. Examples of such proteins include, for example, extracellularly releasable proteins which comprise a polypeptide, as being an active domain of the above-described GalNAcα2,6-sialyltransferase P-B1 or P-B3 and is responsible for the GalNAcα2,6-sialyltransferase activity, and catalyze the GalNAcα2,6-sialic acid transfer.

The sialyltransferases so far cloned have domain structures similar to those of other glycosyltransferases: a short $NH_2$-terminal cytoplasmic tail; a hydrophobic signal-anchor domain; a proteolytically sensitive stem region; and a large COOH-terminal active domain (Paulson, J. C. and Colley, K. J., J. Biol. Chem., 264, 17615–17618, 1989). To determine the location of the transmembrane domain of the GalNAcα2,6-sialyltransferase P-B1 of the present invention, hydropathy plot may be used which can be prepared according to the method of Kyte and Doolittle (Kyte, J. and Doolittle, R. F., J. Mol. Biol., 157, 105–132, 1982). To evaluate a putative active domain, recombinant plasmids introduced with various fragments may be produced and utilized. Exemplary methods will be detailed in the Examples set out below. However, the methods for determination of the location of the transmembrane domain or evaluation of a putative active domain are not limited to the disclosed methods.

For the preparation of the extracellularly releasable protein comprising a polypeptide portion, as being an active domain of the above-described GalNAcα2,6-sialyltransferase P-B1 or P-B3, together with a signal peptide, an immunoglobulin signal peptide sequence, for example, may be used as the signal peptide, and a sequence corresponding to the active domain of GalNAcα2,6-sialyltransferase P-B1 or P-B3 may be fused in-frame to the signal peptide. For example, the method of Jobling et al. (Jobling, S. A. and Gehrke, L., Nature (Lond.), 325, 622–625, 1987) may be applied as such methods, whose specified procedure will be detailed in the Examples of the present specification with respect to GalNAcα2,6-sialyltransferase P-B1. However, types of the signal peptide and methods for ligation of the signal peptide and the active domain are not limited to the aforementioned methods, and a person skilled in the art can suitably choose the polypeptide portion as being an active domain of GalNAcα2,6- sialyltransferase, preferably GalNAcα2,6-sialyltransferase P-B1 or P-B3, and produce the extracellularly releasable protein by ligating the polypeptide portion to any available signal peptide according to an appropriate method. The most preferred example of these proteins is protein SB-690 of the present invention.

According to another embodiment of the present invention, there is provided a process for producing a sialyltransferase which comprises the steps of: (a) expressing a sialyltransferase in a microorganism; (b) extracting the sialyltransferase with about 5 to 9 M urea from proteinic aggregate or precipitate containing the enzyme and being accumulated inside the microorganism; (c) diluting the extract obtained by the above step (b) with a renaturation composition to obtain a primary dilution containing about 1 to 4 M urea; (d) diluting the primary dilution obtained by the above step (c) with a renaturation composition to obtain a secondary dilution containing about 0.5 to 2 M urea; and (e) removing urea from the secondary dilution obtained by the above step (d) by dialysis to afford a renatured sialyltransferase. As described above, sialyltransferases share the common domain structure, and therefore, the preparation process of the present invention may be applicable to any type of sialyltransferase. For example, GalNAcα2,6-sialyltransferase or Galβ1,4GalNAcα2,6-sialyltransferase of the present invention can be suitably prepared by the process of the present invention.

According to an embodiment of the process of the present invention, 8 M urea is used in the step (b); a primary dilution containing about 2 to 3 M urea is obtained in the step (c); a secondary dilution containing about 1 to 2 M urea is obtained in the step (d); and the secondary dilution is dialyzed in the presence of divalent cations in the step (e). According to another embodiment of the present method, 8 M urea is used in the step (b); a primary dilution containing about 2 to 3 M urea is obtained by being left stand for 12 hours or more at 4° C. after primary dilution in the step (c); a secondary dilution containing about 1 to 2 M urea is obtained by being left stand for 48 hours or more after secondary dilution in the step (d); and the secondary dilution is dialyzed in the presence of divalent cations in the step (e). In addition, it is also a preferred method in which the renaturation composition used in the step (c) contains 1 to 2 M urea, 20 mM MOPS-NaOH, 0.5 M NaCl, 20 mM lactose, 0.5 mM EDTA (pH 7.0) and the renaturation composition used in the step (d) contains 20 mM MOPS-NaOH, 0.5 M NaCl, 20 mM lactose, 0.5 mM EDTA (pH 7.0).

The first step of the process for the preparation of sialyltransferase according to the present invention is the expression of a sialyltransferase in microorganisms. To this end, previously cloned genes of sialyltransferases can be used. As cDNAs encoding sialyltransferases, the cDNA encoding Galβ1,4GlcNAc-α2,6-sialyltransferase (Galβ4GlcNAc-α6ST, see, Weinstein et al., Grundmann et al., Bast et al. and Hamamoto et al., supra), the cDNA encoding Galβ1,3(4) GlcNAcα2,3-sialyltransferase (Galβ3(4)GlcNAcα3ST, see, Wen et al. and Kitagawa et al., supra), the cDNA encoding Galβ1,3GalNAc/Galβ1,4GlcNAcα2,3-sialyltransferase (see, Sasaki et al., supra), the cDNA encoding Galβ1, 3GalNAcα2,3-sialyltransferase (Galβ3GalNAc-α3ST, see, Gillespie et al. and Japanese Patent Unexamined Publication No. 5-504678/1993; and Lee et al., supra), for example, may be used, as well as cDNAs encoding the GalNAcα2,6-sialyltransferases of the present invention. Sialyltransferase genes contained in these nucleotide sequences, per se, may be used for the expression of the naturally-derived enzymes.

According to the present invention, in addition to the naturally-derived sialtransferases mentioned above, non-natural sialyltransferases in which the polypeptide sequences of the naturally-derived sialyltransferases are partly deleted or modified may be expressed in microorganisms. For example, since sialyltransferases have a hydrophobic segment (transmembrane domain) in the $NH_2$-terminal region, and sialyltransferases in soluble forms wherein the hydrophobic segment is deleted are preferably expressed in the microorganisms. In addition, deletion of both of the hydrophobic segment and the cytosol segment is also preferred.

In order to produce recombinant vectors for the expression of sialyltransferases, the entire sequences or partial regions of the genes of naturally derived sialyltransferases may be selectively amplified by, for example, PCR method. For example, a sialyltransferase gene (a PCR fragment) may be readily prepared which has an initiation codon and a cloning site and lacks the cytosol domain and transmembrane domain. This type of sialyltransferase genes are suitably used for the introductions into vectors for microbial expressions due to the presence of the initiation codon and the cloning site. In addition, said genes are preferred since they encode non-natural sialyltransferases, in which a part of the polypeptide sequence of the naturally-derived sialyltransferase is deleted, and express non-natural soluble sialyltransferase in microorganisms.

According to the process of the present invention, microorganisms such as *Escherichia coli* may be used for the expression of sialyltransferase. A microbial expression vector suitably used for transformation of such microorganisms may be suitably selected by an ordinarily skilled artisan. For example, where *E. coli* JM109(DE3) or the like is used as the microorganism, microbial expression vectors such as pET3b (Studier, F. W. et al., Method. Enzymol., 185, pp.60–89, 1990) may be used. Methods for introducing the above described sialyltransferase genes into microbial expression vectors and methods for transforming microorganisms with recombinant vectors are both well known to those skilled in the art.

The transformants can be cultured according to methods for culturing transformed microorganisms well known to those skilled in the art. For efficient expression of a desired sialyltransferase in microbial cells, replication of the recombinant protein can be initiated by, for example, the induction of T7-RNA polymerase during the logarithmic growth phase of the transformants. A large amount of naturally-derived or non-natural sialyltransferase is expressed inside the transformants thus obtained, which generally forms proteinic aggregate or precipitate.

The second step of the process of the present invention is the extraction step of a sialyltransferase with 5 to 10 M urea from the proteinic aggregate or precipitate which is accumulated inside the cells and contains the sialyltransferase. In order to expose the proteinic aggregate or precipitate to outside of the microorganisms for its separation, the cultured transformants can be treated with, for example, lysozyme or Triton X-100 and then insoluble fractions may be collected by centrifugation. After then, the precipitates are suspended in a buffer (for example, 10 mM Tris-HCl, pH 7.4) at a protein concentration of about 1 to 10 mg/ml and are subjected to extraction with urea.

For example, solid urea is added to the suspension so as to be 5 to 10 M, preferably 8 M of final concentration, and the precipitates are subjected to extraction for 15 minutes to 2 hours, preferably 30 minutes at 4 to 25° C., preferably at 10° C. While not bound by any specific theory, the hydrophobic portion of a sialyltransferase contained in the extract is exposed by the action of urea, and as a result, a solubilized sialyltransferase is extracted from the proteinic aggregates or precipitates.

Then, an extract solution containing a denatured sialyltransferase can be obtained by removing the precipitates by, for example, centrifugation of the extract at 12,000×g for 15 minutes. This extract normally contains about 0.5 mg/ml of proteins. For example, when 5.7 M urea is used for the extraction, about 80% of proteins can be recovered. Furthermore, upon the extraction, NaCl and Tris-HCl (pH 7.4) are preferably added so that their final concentrations of 0.3 M and 20 mM, respectively, are achieved. Exemplary procedure of the extraction will be explained in detail in the Examples set out below.

The sialyltransferase contained in the extract exposes hydrophobic portions and its higher-order structure is damaged. According to the process of the present invention, renaturation of the sialyltransferase contained in the extract is performed as the third step. The term renaturation herein used means restoration of the higher-order structure of the protein that is lost during the extraction step and the entire or partial recovery of the enzymatic activity. This step is characterized in that the extract is diluted stepwise with a renaturation composition so that the urea concentration can be gradually lowered to efficiently achieve the renaturation of the sialyltransferase.

The renaturation process comprises the steps of, for example, diluting the extract with a renaturation composition to obtain a primary dilution containing about 1 to 4 M urea; diluting the primary dilution with a renaturation composition to obtain a secondary dilution containing about 0.5 to 2 M urea; and removing the urea from the secondary dilution by dialysis to afford a renatured sialyltransferase.

A preferred embodiment of the process comprises the steps of, for example, diluting the extract with a renaturation composition to obtain a primary dilution containing about 2 to 3 M urea; diluting the primary dilution with a renaturation composition to obtain a secondary dilution containing about 1 to 2 M urea; and removing the urea from the secondary dilution by dialysis in the presence of one or more divalent cations to afford a renatured sialyltransferase. A further preferred embodiment is a process comprises the steps of, for example, diluting the extract with a renaturation composition and the result is allowed to stand for 12 hours or more at 4° C. to obtain a primary dilution containing about 2 to 3 M urea; diluting the primary dilution with a renaturation composition and the result is allowed to stand for 48 hours or more to obtain a secondary dilution containing about 1 to 2 M urea; and removing the urea from the secondary dilution by dialysis in the presence of one or more divalent cations to afford a renatured sialyltransferase.

As the renaturation composition, for example, 2 M urea, 20 mM MOPS-NaOH (MOPS: 3-morpholinopropanesulfonic acid) (pH 7.0), 0.5 M NaCl, 10 mM lactose, 0.5 mM EDTA; and 2 M urea, 20 mM Tris-HCl, 0.3 M NaCl, 20 mM lactose, 0.5 mM EDTA (pH 7.4) may be used. In addition, a modified composition may be used in which the components of the latter composition may be changed to, for instance, 20 mM Tris-HCl (pH 8.0); 20 mM MOPS-NaOH (pH 7.0); 20 mM MES-NaOH (pH 6.0) (MES: 3-morpholinoethanesulfonic acid); 0.5 M NaCl; 0.1 M NaCl; or 1 M urea. Furthermore, compositions not containing urea or lactose may also be used. Among these, 2 M urea, 20 mM MOPS-NaOH, 0.5 M NaCl, 20 mM lactose, 0.5 mM EDTA (pH 7.0) is preferably used. When the concentration of NaCl is below 0.1 M, or pH exceeds 9, renaturation efficiency is undesirably reduced. Generally, a salt concentration of 0.3 to 0.5 M and pH of 6 to 8 are preferred after the addition of the renaturation composition.

The first dilution comprises the step of preparing a primary dilution using the aforementioned renaturation composition so that a final protein concentration of the extract is 0.01 to 0.05 mg/ml, preferably about 0.02 mg/ml. For example, the extract may be diluted 10 to 40-fold, preferably about 20-fold, and a urea concentration may be 1 to 4 M, preferably not higher -than about 3 M and not lower than about 2 M. Dilution treatment is generally and preferably performed at 4° C. This primary dilution mixture is left stand for 12 hours or more at 4° C., most preferably for about 12 hours, to initiate gradual renaturation.

The secondary dilution is carried out by diluting the primary dilution with an equal volume of renaturation composition, preferably not containing urea, to achieve approximately the half urea concentration. Through this dilution, urea concentration of the secondary dilution should be lowered to about 0.5 to 2 M, preferably not higher than about 2 M and not lower than 1 M (e.g., 1 to 2 M), and most preferably at about 1.2 M. The secondary dilution is allowed to stand for 40 hours to 2 weeks, preferably 48 to 72 hours, most preferably about 48 hours at 4° C., to proceed gradual renaturation.

After then, to achieve perfect renaturation, the above-obtained secondary dilution is dialyzed against, for example, a renaturation composition free from urea to completely remove remaining urea. The dialysis may be carried out at 4° C. for about 48 hours. Dialysis solution may be, for example, any one of buffer solutions in which the sialyltransferase can be stored stably, as well as the renaturation composition.

In addition, by carrying out the primary and secondary dilution and the final dialysis in the presence of one or more divalent cations, renaturation efficiency can be further improved. Examples of the divalent cations include, for example, magnesium ions and manganese ions. These ions may be used at a concentration of 1 to 10 mM, preferably about 5 mM. It is particularly preferred that the dialysis is performed in the presence of one or more divalent cations. When a reducing agent such as dithiothreitol and mercaptoethanol is added before complete removal of urea in the final dialysis step, the enzymatic activity may occasionally be lost. However, after the urea is completely removed, the enzyme restores resistance to the reducing agent to exhibit the sialyltransferase activity.

The present invention will be further explained more specifically by referring Lo the following examples. However, the scope of the present invention is not limited to these examples.

EXAMPLES (A) Preparation of GalNAcα2,6-sialyltransferase P-B1

In order to obtain a cDNA clone of GalNAcα2,6-sialyltransferase P-B1, PCR with two degenerate oligonucleotides (ST-107 and ST-205) was performed using chick embryo cDNA as a template. A fragment of the desired size of approximately 150 bp was obtained. Among the PCR recombinants, one clone, designated as CEB1, was found to have unique amino acid sequence distinct from the known sialylmotifs of Galβ4GlcNAc-α6STRL (residues 180–225), Galβ3(4)GlcNAc-α3STRL (residues 158–203), and Galβ3GalNAc-α3STPS (residues 144–189). The homologies of the sialylmotif of CEB1 with those of Galβ4GlcNAc-α6STRL, Galβ3(4)GlcNAc-α3STRL and Galβ3GalNAc-α3STPS were 56%, 58% and 60%, respectively.

Screening of a 6-day-old chick embryo cDNA library with the cDNA insert from the CEB1 was carried out, and as a result, several cDNA clones were identified. Among them, clone λ CEB-3043 contained a 2.7 kb insert (FIG. 1). To obtain other overlapping clones, a random-primerd cDNA library was again screened by hybridization with the 0.8 kb EcoRl-BglII fragment of the 5'-end of the λ CEB-3043. Fifteen clones were isolated from the cDNA library. Among them, one clone, λ CEBHAD contained a 220 bp insert overlapping with the 5'-end of clone λ CEB-3043 for 160 bp.

The combined DNA from these two cDNAs contained a 1.7 kb of open reading frame that ends at a TGA terminal codon at nucleotide 1699. A poly adenylation signal (AATAAA) at 23 nucleotides upstream from the poly(A) sequence exists at the 3'-end. Translation of this open reading frame affords GalNAcα2,6-sialyltransferase P-B1 of the present invention (occasionally referred to as P-B1 in the examples) of 566 amino acids with a molecular mass of 64,781, which starts with a methionine codon at nucleotide 1 with a conventional initiation sequence (Kozak, M., Nature (Lond.), 308, 241–246, 1984). The cDNA including a gene encoding the GalNAcα2,6-sialyltransferase of the present invention, the nucleotide sequence of λ CEB-3043 as being the gene encoding the GalNAcα2,6-sialyltransferase of the present invention, and the amino acid sequence of the GalNAcα2,6-sialyltransferase P-B1 of the present invention are shown in the SEQ ID No.1 and 5, respectively of the sequence listings.

Polymerase Chain Reaction (PCR)

PCR was performed using degenerate primers [5' primer ST107: TGGGCCTTGGII(A/C)AGGTGTGCTGTTG, and 3' primer ST205: AGGCGAATGGTAGTTTTTG(A/T) GCCCACATC] deduced from conserved regions in Galβ4GlcNAc-α6STRL (Weinstein, J. et al., J. Biol. Chem., 262, 17735–17743, 1987), Galβ4GlcNAc-α6STHP (Grundmann, U. et al., Nucleic Acids Res., 18, 667, 1990), and Galβ3GalNAc-α3STPS (Gillespie, W. et al., J. Biol. Chem., 267, 21004–21010, 1992). To obtain cDNA, poly (A)-rich RNA (2 μg) from 3 day-old chick embryos was incubated with an oligo-dT primer (Pharmacia), 1 mM each of dATP, dCTP, dGTP and dTTP, and 2 U/μl of RNase inhibitor (Promega) in 10 mM Tris-HCl (pH 8.3), 50 mM KCl, 1.5 mM $MgCl_2$ and 0.001% gelatin in 50 μl for 10 min at 0° C., and then for further incubation was carried out for 60 min at 42° C. after the addition of 100 μU Moloney murine leukemia virus reverse transcriptase (BRL).

After heating the reaction mixture at 94° C. for 3 min, cDNA prepared from 0.2 μg of poly(A)-rich RNA was used for the PCR experiment in a mixture comprising 10 mM Tris-HCl (pH 8.3), 50 mM KCl, 1.25 mM $MgCl_2$, 0.001% gelatin, 200 μM of each dATP, dCTP, dGTP and dTTP, 2 U of Taq DNA polymerase (Promega), and 40 pmoles of each PCR primer in 50 μl. PCR amplification, 35 cycles, was carried out, each cycle consisting of denaturation at 96° C. for 45 sec, annealing at 50° C. for 60 sec, and extension at 72° C. for 60 sec. The PCR products were developed on a 3% agarose gel. The DNA fragment corresponding to 150 bp was eluted from the gel (Qiaex kit; Qiagen), blunt-ended and kinated, and then subcloned into the SmaI site of pUC119, and finally sequenced.

Construction of a cDNA Library

Total RNA was prepared from chick embryos (6-day-old) by the guanidinium thiocyanate method, followed by centrifugation in a 5.7 M CsCl solution (Sambrook, J., Molecular Cloning: a Laboratory Manual, 2nd ed. Cold Spring Harbor Laboratory, Cold Spring Harbor, N.Y. 1989). Poly (A)-rich RNA was purified with oligotex-dT30 (Takara), and then employed for the construction of a cDNA library using λ ZAPII (Stratagene) and cDNA synthesis (Pharmacia) kits with an oligo-dT primer and random primers.

Screening of the cDNA Library

The amplified cDNA library ($1 \times 10^6$ plaques) was screened with the chick embryo PCR fragments. The plaque-transferred filters were hybridized with $^{32}$P-radiolabeled DNA probes for 12 h at 65° C. in 5×SSC, 0.02% SDS, 5×Denhardt's solution and 10 μg/ml denatured salmon sperm DNA, and then washed twice at 65° C. for 20 min in 2×SSC, 0.1% SDS. To obtain plasmids from the isolated phage clones, phagemid rescue was performed according to the manual of the manufacturer of the λ ZAPII cloning kit (Stratagene). cDNA inserts were excised directly as Bluescript plasmids. Plasmids were produced by the standard molecular cloning method according to Sambrook et al. (Sambrook, J. et al., Molecular Cloning: a Laboratory Manual).

DNA Sequence Analysis

The DNA sequences of the inserts were determined by the dideoxy-chain termination method (Sanger, F. et al., Proc. Natl. Acad. Sci. USA, 74, 5463–5467, 1977) using single-strand DNA as a template for T7-DNA polymerase. The sequencing reaction and electrophoresis were carried out using the AutoRead DNA sequencing kit and a DNA sequencer (Pharmacia). Single strand DNA was prepared from *Escherichia coli* XL-Blue (Stratagene) after superinfection with helper phage R408 (Stratagene). The sequence data were analyzed with a computer using PC/Gene (Teijin System Technology).

Northern and Southern Blot Analyses

To confirm the existence of the gene, Southern blot analysis of chick genomic DNA was performed. Hybridization with the EcoRI cDNA insert of λ CEB-201 gave a single band for the DNA digested with EcoRI and BamHI, and two bands for the DNA digested with HindIII and SacI. This simple hybridization pattern indicates that the cloned cDNA is a single copy gene.

The transcription pattern during embryonic development was examined by Northern blot hybridization. Analysis of RNA from 6, 8 and 10 day-old chick embryos revealed two RNA species of 3.0 and 2.2 kb. The 3.0 kb transcript was abundant and constantly expressed during all embryonal stages. A low level of the 2.2 kb transcript was detected in 6 day-old embryos and its expression was decreased in 8 and 10 day-old embryos. The gene expression was analyzed using 10 μg poly(A)-rich RNA obtained from various chicken tissues: brain, heart, liver, lung, kidney, and testis. Very low levels of the 3.0 and the 4.0 kb transcripts was detected in testes, while almost no signals were detected in other tissues. The following description details each of the experiments.

For Northern blots, 5 μg of denatured poly(A)-rich RNAs from chick embryo was size-fractionated on formaldehyde-agarose gels and then blotted onto Hybond N+ nylon membranes (Amersham). For Southern blots, 7.5 μg of genomic DNA prepared from chick embryos was digested with restriction enzymes EcoRI, BamHI, HindIII and SacI, and then size-fractionated on 0.6% agarose gels. After electrophoresis, the gels were denatured (30 min) in 0.5 N NaOH and 1.5 M NaCl and neutralized (30 min) in 0.5 M Tris-HCl (pH 7.5) and 1.5 M NaCl, and then the DNA was transferred onto Hybond N+ nylon membranes. Both Northern and Southern filters were prehybridized in 50% formamide, 5×SSC, 5×Denhardt's, 0.5% SDS, and 10 μg/ml denatured salmon sperm DNA at 37° C. for 1 h, and then hybridized with a $^{32}$P-labelled DNA probe for 12 h under the same conditions as for prehybridization. The probe applied was a 0.6 kb EcoRI cDNA insert of λ CEB-201, which was labeled with a Multiprime Labeling System (Amersham). The filters were washed twice for 10 min at 65° C. in 2×SSC and 0.1% SDS, followed by washing twice with 0.2×SSC and 0.1% SDS at 65° C. for 30 min, and then exposed to Kodak XAR film for about one day at −70° C.

The amino acid sequence of the sialyltransferase P-B1 of the invention, which was revealed as described above, shows the following characteristic features that are not observed in sialyltransferases so far known.

(i) All of the sialyltransferases previously cloned are critical Type II membrane proteins. They have a domain structure similar to that of other glycosyl-transferases: a short $NH_2$-terminal cytoplasmic tail; a hydrophobic signal-anchor domain; a proteolytically sensitive stem region; and a large COOH-terminal active domain. On the other hand, the sialyltransferase P-B1 of the invention has a large stem region (or intermediate region).

(ii) The sialyltransferase P-B1 of the invention has a PEST region (residues 233–258). It has been known that the amino acid sequences of proteins with intracellular half-lives of less than 2 hours contain one or more regions that are rich in proline, glutamic acid, serine, and threonine residues (referred to as PEST: Rogers, S. et al., Science, 234, 364–368, 1986). These PEST regions are generally flanked by clusters containing several positively charged amino acids. Other sialyltransferases previously known do not have this region.

(iii) Two stretches of eight amino acids (SSSXVSTC) were found at residues 247–254 and 330–337. A search of the Genebank database for other proteins revealed no sequence similarity to this sequence.

Sialyltransferases so far known exhibit remarkable tissue-specific expression, which seems to be correlated with the existence of cell type-specific carbohydrate structures (Paulson, J. C. and Colley, K. J., J. Biol. Chem., 264, pp.17615–17618, 1989). The results of Northern blotting indicates that the pattern of expression of sialyltransferase P-B1 apparently changes. The transcriptions of three different sizes of mRNAs (4.0, 3.0 and 2.2 kb) from the sialyl-transferase P-B1 gene suggests that they are generated through alternative splicing and alternative promoter utilization mechanisms as observed for Galβ1,4GlcNAcα2,6-sialyltransferase (Galβ4GlcNAc-α6STRL) and Galβ1,3(4) GlcNAcα2,3-sialyltransferases (Galβ3(4)GlcNAc-α3STRL, Weinstein, J. et al., J. Biol. Chem., 262, 17735–17743, 1987; and Wen, D. X. et al., J. Biol. Chem., 267, 21011–21019, 1992). This hypothesis is supported by the results of Southern hybridization, which showed the existence of a single copy gene for sialyltransferase P-B1.

(B) Preparation of the Soluble Form Protein SB-690

In order to utilize the GalNAcα2,6-sialyltransfer activity of the GalNAcα2,6-sialyltransferase P-B1 of the present invention, protein SB-690 in a soluble form was prepared which retains the activity of the present enzyme and is released from the cells upon expression.

Figure 2:
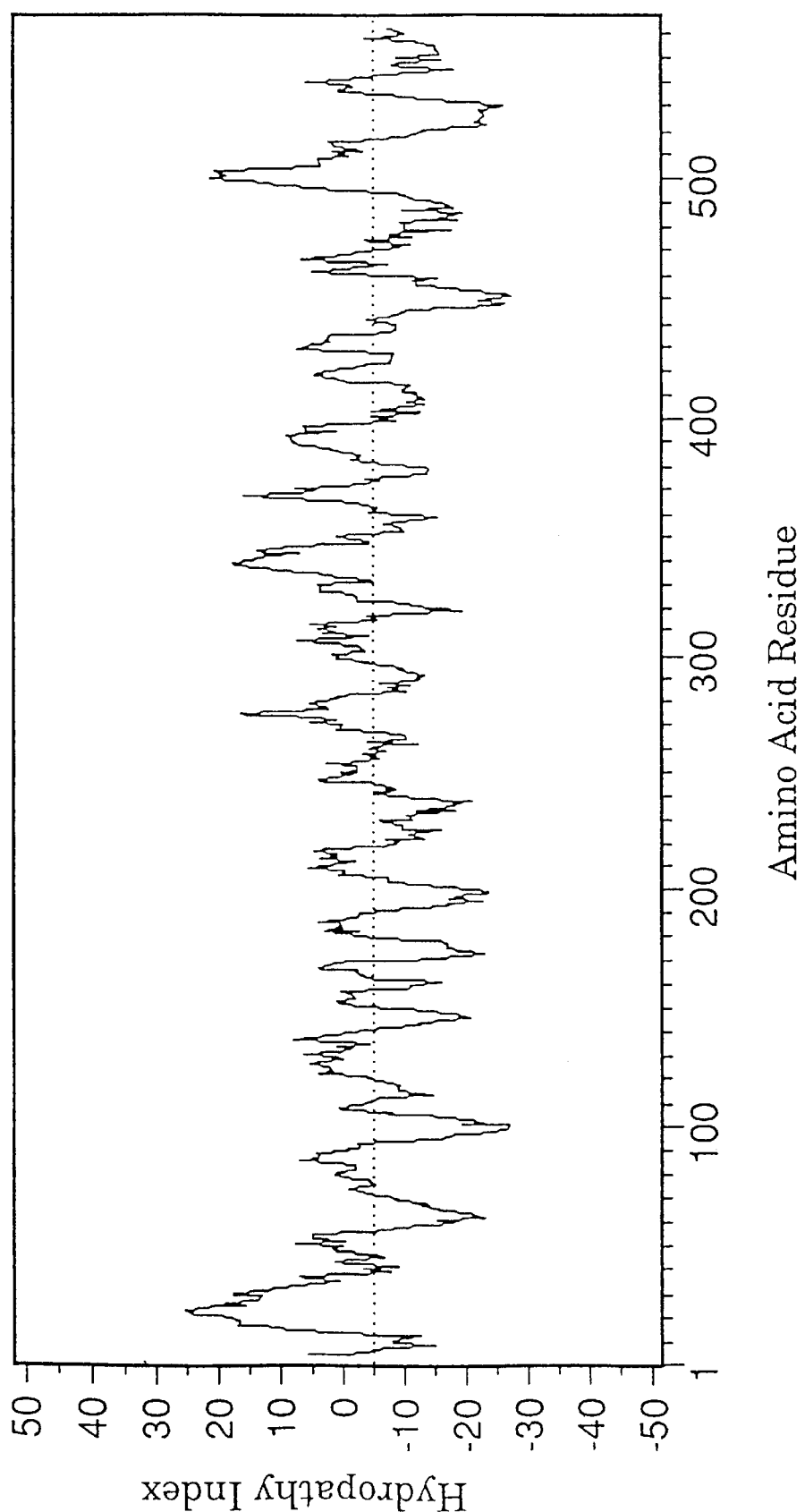
FIG. 2 shows the result of hydrophobicity analysis of the GaINAcα2,6-sialyltransferase P-B1 according to the present invention. In the figure, N-terminus of the protein is depicted at the left side and positive values indicate hydrophobic regions.

The sialyltransferases so far cloned have a domain structure similar to that of other glycosyl-transferases: a short $NH_2$-terminal cytoplasmic tail; a hydrophobic signal-anchor domain; a proteolytically sensitive stem region; and a large COOH-terminal active domain. To determine the location of any transmembrane domain of GalNAcα2,6-sialyltransferase of the present invention, a hydropathy plot (FIG. 2) was prepared from the translated sequence according to the method of Kyte and Doolittle (Kyte, J. and Doolittle, R. F., J. Mol. Biol., 157, 105–132, 1982). As as result, it is suggested that a critical hydrophobic transmembrane domain of GalNAcα2,6-sialyltransferase P-B1 of the present invention consists of 21 amino acids residues from the amino acid No.17 to 37.

Figure 3:
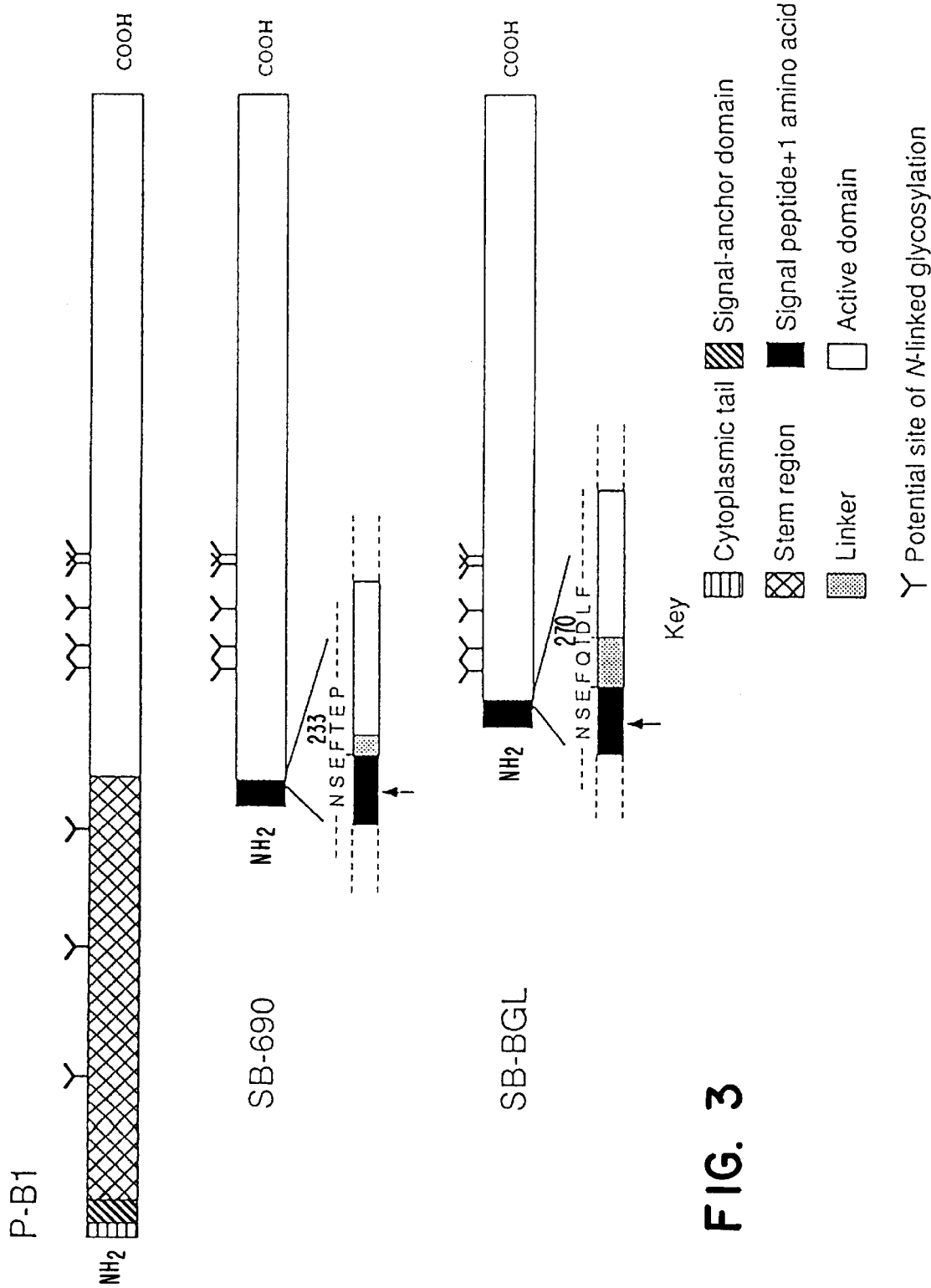
FIG. 3 shows the location of the active domain of the GalNAcα2,6-sialyltransferase P-B1 according to the present invention and the result of comparison with the structure of protein SB-690 which has GalNAcα2,6-sialyltransferase activity and can be extracellularly released. In the figure, protein SB-BGL is a protein not having GalNAcα2,6-sialyltransferase activity.

As described above, the hydrophobic signal anchor domain of GalNAcα2,6-sialyltransferase is located from amino acid residues No.17 to 37. Residues from 233 to 269 apparently contain certain essential residues for the enzymatic activity, because the media from cells transfected with pcDSB-BGI, had no significant activity, while the protein (33 KDa) was synthesized in an in vitro translation/transcription system with pSB-BGL as a template. The active domain was thus deduced to be around 233–566 (FIG. 3), which is a comparative size to that of other cloned sialyltransferases. In order to produce the soluble protein containing the active domain described above, the sequence relating to the putative active domain of P-B1 was in-frame fused to the sequence of immunoglobulin signal peptide (Jobling, S. A. and Gehrke. L., Nature (Lond.), 325, 622–625, 1987). Details of the experiments are shown below.

A vector plasmid PUGS was constructed by replacing the PstI-XhoI fragment of the p Bluescript SK(+) plasmid with a 117 bp of a synthetic DNA fragment. This fragment contains 43 bp of the 5'-untranslated leader sequence of Alfalfa Mosaic Virus (Jobling, S. A. and Gehrke, L., Nature (Lond.) 325, 622–625, 1987) with a synthetic PstI site at the 5'-end, followed by the mouse immunoglobulin M heavy chain signal peptide sequence (57 bp) (Boersch-Supan, M. E. et al., J. Exp. Med. 161, 1272–1292, 1985) with a 17 bp of a synthetic EcoRI, BglII and XhoI cloning site at the 3'-end. The nucleotide sequence of this fragment is 5'-CTGCAGGGTTTTTATTTTTAATTTTCTTTCAAATA CTTCCACCATGAAATTCAGCTGGGTCAT-GTTCTTCCTGATGGCAGTGGTTA-CAGGGGTCAATTCAGAA TTCCAGATCTCGAG-3'.

λ CEB-3043 encoding GalNAcα2,6-sialyltransferase of the present invention was partially digested with EcoRV, and 1.8 kb fragment was subcloned into EcoRV site of pBlue-script SK(+) to generate pCEB-1800. This clone lacks 0.8 kb of 3'-untranslated region of λ CEB-3043. An active domain of GalNAcα2,6-sialyltransferase P-B1 was generated by PCR using the 5'-primer, 5'-AGGGCTGCTGAATTCACTGAGCCACAG-3' (nucleotides 679–708), with a synthetic EcoRI site at the middle of the primer and a 3' universal M13 sequencing primer and pCEB-1800 as a template. The PCR product was digested with EcoRI and XhoI, and then ligated into the EcoRI/XhoI site of PUGS to yield the plasmid pSB-690. In this plasmid, a sequence obtained by in-frame fusion of the 3'-end of the immunoglobulin signal sequence to the putative active domain of GalNAcα2,6-sialyltransferase P-B1 was contained. The fusion fragment was excised from pSB-690 with PstI and XhoI, and then inserted into the PstI/XhoI site of expression vector pcDSR α to yield pcDSB-690.

As a control, protein SB-BGL which lacks the active domain of GalNAcα2,6-sialyltransferase was produced as described below. pCEB-1800 and PUGS were digested with BglII, and the protruding ends were filled by using the Klenow fragment of DNA polymerase. After heat denaturation of the Klenow fragment of DNA polymerase (at 94° C. for 20 min), these plasmids were digested with XhoI. The 1.0 kb fragment from pCEB-1800 was gel purified and subcloned into the blunt-ended BglII/XhoI site of PUGS to yield pSB-BGL. The PstI/XhoI fragment from PSB-BGL was subcloned into the PstI/XhoI site of pcDSR α to generate pcDSB-BGL.

Expression of the above described protein was performed as follows. COS-7 cells were transiently transfected with 5 µg of plasmid DNA using the DEAE-dextran method (McCutchan, J. H. and Pagano, J. S. J. Natl. Cancer Inst. 41, pp.351–357,1968). The media were harvested after 48 h transfection and then concentrated 10 times on Centricon 30 filters (Amicon) for the enzyme assay. For metabolic labeling, COS cells (60-mm culture dish) were washed with Met-free medium (Dulbecco's modified Eagle's medium and 2% fetal calf serum) (GIBCO) and then incubated for 1 h with the same media. The cells were pulse-labeled with 10 MBq/dish of Express $^{35}$S protein labeling mix (Du Pont-New England Nuclear) in 1.5 ml of Met-free media for 2 h. These cells were then washed with Met-free media and chased for 5 h in media without Express-label. The media containing secreted proteins were harvested, concentrated 10 times, and then subjected to SDS-PAGE, followed by fluorography.

The enzyme activity of the expressed protein was measured as follows. The assays using oligosaccharides and glycoproteins as acceptors were performed in the presence of 50 mM sodium cacodylate buffer (pH 6.0), 50 µM CMP-[$^{14}$C-]NeuAc (0.9 Bq/pmol), 1 mg/ml of bovine serum albumin, 2 mg/ml of acceptor substrate and 1 µl of concentrated COS cell medium, in a final volume of 10 µl, and were incubated at 30° C. for 2 h. At the end of the incubation period, 1 µl of the assay mixture was applied to a Silica gel 60HPTLC plate (Merck, Germany). The plate was developed with ethanol:pyridine:n-butanol:water:acetate (100:10:10:30:3), and the radioactivity was visualized and quantified with a BAS2000 radio image analyzer (Fuji Photo Film, Japan). The radioactivity remaining at the origin was taken as sialylated glycoprotein.

Identification of the sialylated products was carried out as follows. Asialo-BSM were resialylated with CMP-[$^{14}$C] NeuAc in pcDSB-690 COS cell medium and β-elimination oligosaccharides were prepared. β-elimination was carried out according to Carlson's method (Carlson, D. M., J. Biol. Chem., 243, 616–626, 1968). Asialo-BSM (100 µg each) was sialylated with CMP-[$^{14}$C]NeuAc in pcDSB-690 COS cell medium under the same conditions as above, except that the incubation period was 12 h. The reaction was terminated by adding 500 µl of 1% phosphotungstic acid in 0.5 M HCl, followed by centrifugation at 10,000×g for 5 min. The pellets were washed once with the same phosphotungstic acid solution and once with methanol, dissolved in 0.5 ml of 0.05M NaOH and 1 M NaBH$_4$, and then incubated 30 h at 45° C.

At the end of the incubation period, the solution was neutralized with acetic acid to pH 6 and then lyophilized. The dehydrated products were dissolved in 50 µl of water, and then desalted by gel filtration on a Sephadex G-15 column (0.5×5 cm) equilibrated and eluted with water. The radioactive fractions were subjected to thin layer chromatography for identification of the products without further purification. NeuAcα2,6GalNAc-ol and GlcNAcβ1,3 [NeuAcα2,6]GalNAc-ol from native BSM in two different developing solvent were co-migrated. The ratio of the transferred sialyl residue was 1:0.9:0.6. The results of the co-migration of Sialylated GalNAc-SerNAc with with NeuAcα2,6GalNAc-SerNAc in the two different solvent systems indicate that the protein SB-690 of the present invention forms the NeuAcα2,6 linkage to GalNAc that is directly attached to Ser or Thr residues in glycoproteins.

Media from cells transfected with pcDSB-690 contained sialyltransferase activity and it provide strong evidence that the protein SB-690 of the present invention expressed by pcDSB-690 was secreted out of cells while retaining sialyltransferase activity. On the other hand, media obtained from cells transfected with cDSB-BGL had no sialyltransferase activity.

The acceptor specificity of the protein SB-690 of the present invention was examined with the concentrated COS-7 cell culture medium transfected with pcDSB-690. As shown in Table 1, asialo-mucin, fetuin and asialo-fetuin served as good acceptors. Remarkably, fetuin was shown to be a better acceptor than asialo-fetuin (Baubichon-Cortay, H. et al., Carbohydr. Res., 149, 209–223, 1986; and Brockhausen, I. et al., Biochemistry, 29, 10206–10212, 1990). Other glycoproteins, oligosaccharides and glycolipids did not serve as acceptors, except GalNAc-SerNAc. These data suggest that the acceptor site is GalNAc directly attached to Ser or Thr residues in glycoproteins through an α-glycoside linkage.

TABLE 1

Acceptor specificity of the protein SB-690 of the invention

| Acceptor | Pmoles/hr/10µ 1 medium |
| --- | --- |
| Fetuin | 142 |
| Asialo-fetuin | 96 |
| α 1 acid glycoprotein | 6 |
| Asialo- α 1 acid glycoprotein | 4 |
| Bovine submaxillary mucin | 15 |
| Bovine submaxillary asialo-mucin | 186 |
| Ovomucoid | 7 |
| Asialo-ovomucoid | 0 |
| Gal β 1,3GlcNAc β 1,3Gal β 1,4Glc | 0 |
| Gal β 1,4GlcNAc | 0 |
| Gal β 1,3GalNAc | 0 |
| GalNAc β 1,4 Gal | 0 |
| Gal β 1,4Glc | 0 |
| Galactose | 0 |
| Ganglioside mixture | 0 |
| Ganglioside GD1a | 0 |
| GalNAc-SerNAc | 4 |
| Benzyl-GalNAc | 2 |

*A number of 0 indicates less than 1 pmol/hr/10µ 1 medium.

So far cloned sialyltransferases only exhibit acceptor specificity for the Gal-moiety. While the GalNAcα2,6-sialyltransferase P-B1 and protein SB-690 of the present invention exhibit acceptor specificity for the GalNAc- but not the Gal-moiety. The following evidence supports that GalNAcα2,6-sialyltransferase P-B1 and the protein SB-690 of the present invention have the activity of GalNAcα2,6-sialyltransferase, which transfer CMP-NeuAc with an α2,6-linkage onto a GalNAc residue O-linked to Thr/Ser of a glycoprotein:

(i) The expression of pcDSB-690 in COS cells reveals the remarkable acceptor specificity for only the GalNAc moiety bound to Ser/Thr residues, while no detectable enzyme activity was found toward the other substrates tested (Table 1).

(ii) The sialylated products obtained from bovine submaxillary asialo-mucin and GalNAc-SerNAc were shown to have sialic acid bound to the GalNAc moiety through an α2,6-linkage.

The two types, i.e., bovine submaxillary gland- and liver (brain)- types, of GalNAc-α6ST were reported, which have the different acceptor specificity (Bergh, M. E. et al., J. Biol. Chem., 258, 7430–7436, 1983). The former enzyme has the broad specificity toward GalNAc, Galβ1,3GalNAc and NeuAcα2,3Galβ1,3GalNAc, whereas the latter has only toward NeuAcα2,3Galβ1,3GalNc moiety of glycoproteins. The acceptor specificities of the GalNAcα2,6- sialyltransferase P-B1 and the protein SB-690 of the present invention were found to be similar to that of the former enzyme.

Examination of the acceptor site of asialo-mucin showed that NeuAcα2,6GalNAc-Ser/Thr was the most abundant product. However, considering the ratio of glycoconjugates in bovine submaxillary asialo-mucin, i.e., GalNAc-Ser/Thr, GlcNAcβ1,3GalNAc-Ser/Thr, and Galβ1,3GalNAc-Ser/Thr amounted to 65%, 25%, and 5%, respectively (Tsuji, T. and Osawa, T., Carbohydr. Res., 151, pp.391–402, 1986), GalNAcα2,6-sialyltransferase P-B1 and the protein SB-690 of the present invention seem to have the following acceptor preference: Galβ1,3GalNAc-Ser/Thr>GlcNAcβ1,3GalNAc-Ser/Thr>GalNAc-Ser/Thr. On the other hand, the facts that almost all the radioactivity was released on weak alkali treatment and that fetuin is preferred over asialo-fetuin (Table 1) indicate that NeuAcα2,3Galβ1,3GalNAc-Ser/Thr is a preferred substrate over Galβ1,3GalNAcα-Ser/Thr, as reported for calf liver (Bergh, M. E. et al., J. Biol. Chem., 258, 7430–7436, 1983) and rat brain (Baubichon-Cortay, H. et al., Carbohydr. Res., 149, 209–223, 1986) GalNAcα2,6-sialyltransferases.

The sialylation of GalNAc-SerNAc was much slower than that of corresponding residues on asialo-mucin (Table 1). Brockhausen et al. (Brockhausen et al., Biochemistry, 29, 10206–10212, 1990) showed that a length of at least five amino acid is required for efficient synthetase activity. A similar effect of the peptide portion directly on GalNAcα2,6-sialyltransferase P-B1 and the protein SB-690 of the present invention is also suggested from this observation (Table 1).

The regents and the like used in the above preparation examples (A) and (B) were as follows: Fetuin, asialo-fetuin, bovine submaxillary mucin, α1-acid glycoprotein, galactose β1,4-N-acetylgalactosamine, CMP-NeuAc, lacto-N-tetraose, benzyl-GalNAc, N-acetyllactosamine, and Triton CF-54 were obtained from Sigma (St. Louis, USA). CMP [$^{14}$C]NeuAc(11 Gsq/mmole) was obtained from Amersham (U.K.). N-Acetylgalactosamine β1,4-galactose was a gift from Dr. Kajimoto (The institute of Physical and Chemical Research, RIKEN, Wako-shi, Saitama-ken, Japan). 2-Acetamide and 2-deoxy-galactosyl-αN-acetylserine (GalNAc-SerNAc) were synthesized according to Grundler and Schmidt (Grundler G., and Schmidt R. R., Liebigs Ann. Chem., 1984, 1826–1847, 1984). NeuAcα2,6-GalNAc-SerNAc was prepared from NeuAcα2,6GalNAc-Ser (MECT) by acetylation with anhydroacetate in pyridine-water. NeuAcα2,6GalNAc-ol and GlcNAcβ1,3[NeuAcα2,6]GalNAc-ol were prepared from bovine submaxillary mucin according to Tsuji and Osawa (Tsuji, T. and Osawa T., Carbohydr. Res., 151, 391–402, 1986) and identified by 270 MHz $^1$H and $^{13}$C NMR (Savage, A. V. et al., Eur. J. Biochem., 192, pp. 427–432, 1990; and Savage, A. V. et al., Eur. J. Biochem., 193, 837–843, 1990). Synthetic primers were synthesized with the Applied Biosystem 394 DNA synthesizer. Restriction endonucleases SmaI, EcoRI, BamHI, HindIII, SacI, XhoI, BglII and PstI were from Takara (Japan).

(C) Preparation of GalNAcα2,6-sialyltransferase P-B3

In order to obtain cDNA clones of GalNAcα2,6-sialyltransferases, PCR with two degenerate oligonucleotides (ST-107 and ST-205) was performed with chick embryo cDNA as a template. The fragment of the desired size of approximately 150 bp was purified by agarose gel electrophoresis. As a result of sequencing of the PCR products, it was revealed that they included those encoding Galβ1,4GlcNAcα2,6-sialyltransferase (Kurosawa, N., et al., Eur. J. Biochem., 219, 375–381, 1994) and GalNAcα2,6-sialyltransferase P-B1, as well as a PCR product encoding a novel amino acid sequence, pCRB3. The identity of the sialylmotif of pCRB3 with those of above-mentioned sialyltransferases was 65 through 57%.

In order to identify the complete coding sequence of the gene, a young chicken testis cDNA library was screened with the cDNA insert of pCRB3. The screening about 5×10$^5$ independent clones yielded one positive clone, λ CEB3-T20, which has an insert size of 2.05 kb.

The nucleotide sequence of the cDNA clone included an open reading flame of 1212 bp, coding for 404 amino acids with a molecular mass of 45.8 kDa. The open reading frame starts with a methionine codon at nucleotide 1, with a conventional translation initiation sequence (Kozak, M. Nature, 308, 241–246, 1984), and ends with a TGA stop codon at nucleotide 1213. The open reading flame is flanked by a 5'-untranslated sequence of 384 bp and a 3'-untranslated sequence of 451 bp. The DNA sequence 5' of the initiation site contains stop codons in all three reading frames. The nucleotide sequence and deduced amino acid sequences of λ CEB3-T20 are shown in the SEQ ID No.3 of the sequence listings. The GalNAcα2,6-sialyltransferase having this amino acid sequence was designated as P-B3.

This GalNAcα2,6-sialyltransferase P-B3 (when the GalNAcα2,6-sialyltransferase P-B1 is referred to as ST6GalNAcA, this enzyme is occasionally referred to as ST6GalNAcB) has type II transmembrane domain, containing a 17-amino acid N-terminal hydrophobic sequence bordered by charged residues, as has been found for all sialyltransferases cloned to date. Comparison of the primary sequence of GalNAcα2,6-sialyltransferase P-B3 with other amino acid sequences in DNA and protein data banks revealed similarities in two regions to all of the cloned sialyltransferases.

One region (sialylmotif L) in the center of the GalNAcα2,6-sialyltransferase P-B3, consisting of a 45 amino acid stretch, shows 64–24% sequence identity, whereas the other, in the COOH-terminal portion (sialylmotif S, residues 333–355), exhibits 78–43% identity. The overall amino acid sequence identity of GalNAcα2,6-sialyltransferase P-B3 is 10% to chick Galβ1,4GlcNAcα2,6-sialyltransferase (Kurosawa, N., et al., Eur. J. Biochem., 219, 375–381, 1994), 13% to chick Gaβ1,3GalNAcα2,3-sialyltransferase (Kurosawa N. et al., Bioclem. Biophys. Acta., 1244, 216–222, 1995), and 32% to chick ST6GalNAcA (22), respectively. These results suggest that the cloned gene belongs to the sialyltransferase gene family.

Details of the experiments are as follows.

Polymerase Chain Reaction (PCR)

PCR was performed using degenerate primers [5' primer ST107: TGGGCCTTGGII(A/C)AGGTGTGCTGTTG, and 3' primer ST-205: AGGCGAATGGTAGTTTTTG(A/T)GCCCACATC] deduced from conserved regions in Galβ4GlcNAc-α6STRL (Weinstein, J. et al., J. Biol. Chem., 262, 17735–17743, 1987), Galβ4GlcNAc-α6STHP (Grundmann, U. et al., Nucleic acids Res., 18, 667, 1990), and Galβ3GalNAc-α3STPS (Gillespie, W. et al., J. Biol. Chem., 267, 21004–21010, 1992). To obtain cDNA, poly (A)-rich RNA (2 μg) from 3 day-old chick embryos was incubated with an oligo-dT primer (Pharmacia), 1 mM each of dATP, dCTP, dGTP and dTTP, and 2 U/μl of RNase inhibitor (Promega) in 10 mM Tris-HCl (pH 8.3), 50 mM KCl, 1.5 mM MgCl$_2$ and 0.001% gelatin in 50 μl for 10 min at 0° C., and then for additional 60 min at 42° C. after the addition of 100 μU Moloney murine leukemia virus reverse transcriptase (BRL).

After heating at 94° C. for 3 min, cDNA prepared from 0.2 μg of poly(A)-rich RNA was used for the PCR experiment in a mixture comprising 10 mM Tris-HCl (pH 8.3), 50 mM KCl, 1.25 mM MgCl$_2$, 0.001% gelatin, 200 μM of each dATP, dCTP, dGTP and dTTP, 2 U of Taq DNA polymerase (Promega), and 40 pmoles of each PCR primer in 50 μl. PCR amplification, 35 cycles, was carried out, each cycle consisting of denaturation at 96° C. for 45 sec, annealing at 50° C. for 60 sec, and extension at 72° C. for 60 sec. The PCR products were developed on a 3% agarose gel. The DNA fragment corresponding to 150 bp was eluted from the gel (Qiaex kit; Qiagen), blunt-ended, kinated, and then subcloned into the SmaI site of pUC119, and finally sequenced.

Construction of a cDNA/Library

Total RNA was prepared from chick embryos (6 day-old) by the guanidinium thiocyanate method, followed by centrifugation in a 5.7 M CsCl solution (Sambrook, J., Molecular Cloning: a Laboratory Manual, 2nd edition). Poly(A)rich RNA was purified with Oligotex-dT30 (Takara), and then employed for the construction of a cDNA library using λ ZAPII (Stratagene) and cDNA synthesis kits (Pharmacia) with an oligo-dT primer and random primers.

Screening of the cDNA Library

The amplified cDNA library (1×10$^6$ plaques) was screened with the chick embryo PCR fragments. The plaque-transferred filters were hybridized with $^{32}$P-radiolabeled DNA probes for 12 h at 65° C. in 5×SSC, 0.2% SDS, 5×Denhardt's solution, and 10 μg/ml denatured salmon sperm DNA. The filters were then washed twice at 65° C. for 20 min in 2×SSC, 0.1% SDS. To obtain plasmids from the isolated phage clones, phagemid rescue was performed according to the instructions of the manufacturer of the λ ZAPII cloning kit (Stratagene). cDNA inserts were excised directly as Bluescript plasmids. Plasmids were produced by the standard molecular cloning method according to Sambrook, et al. (Sambrook, J. et al., Molecular Cloning: a Laboratory Manual, 2nd ed.).

DNA Sequence Analysis

The DNA sequences of the inserts were determined by the dideoxy-chain termination method (Sanger, F. et al., Proc. Natl. Acad. Sci. USA, 74, 5463–5467, 1977) using single-strand DNA as a template for T7-DNA polymerase. The sequencing reaction and electrophoresis were carried out using an AutoRead DNA sequencing kit and a DNA sequencer (Pharmacia). Single Strand DNA was prepared from *Escherichia coli* XL-Blue (Stratagene) after superinfection with helper phage R408 (Stratagene). The sequence data were analyzed with a computer using PC/Gene (Teijin System Technology).

To confirm the existence of the gene, Southern blot analysis was performed for chicken genomic DNA. Hybridization of the cDNA insert of pCRB3 for chicken genomic DNA gave a single band on digestion with EcoRI and two bands with BamHI. This simple hybridization pattern indicates that the cloned cDNA was a single copy gene. Southern blot analysis of genomic DNA from mouse and monkey with the pCRB3 probe under low stringency conditions suggested that this gene is conserved across species. For Southern blot, each 7.5 μg of genomic DNA prepared from mouse brain, COS-7 cells and chicken testes were digested with restriction enzyme and then size-fractioned on 0.6% agarose gels.

The mRNA size and distribution of the GalNAcα2,6-sialyltransferase P-B3 gene were determined by Northern blot analysis. Analysis of RNA from 3, 6, 8, 10 and 12-day old embryos revealed two RNA species of 4.5 kb and 2.2 kb. The 4.5 kb mRNA was expressed abundantly at all embryonic stages examined, while not expressed in adult tissues. The less abundant 2.2 kb mRNA was expressed at the early embryonic stage, being abundant at the late embryonic stage and in adult tissues. The size of the 2.2-kb transcript suggests that the obtained cDNA clone (λ CEB3-T20) was close to full length. For Northern blots, 5 μg of poly(A)-rich RNAs from chick embryo and 10 μg of all RNA from chicken tissues were size-fractioned on formaldehyde-agarose gels.

Sialyltransferases previously known exhibit remarkable tissue-specific expression, which is considered to be correlated with the existence of cell type-specific carbohydrate structures (Paulson, J. C. and Colley, K. J., J. Biol. Chem., 264, pp.17615–17618, 1989). The results of Northern blotting indicate that the pattern of expression of sialyltransferase P-B3 changes. The precise structure of embryo-specific 4.5 kb mRNA has not been known. However, the production of two different sizes of mRNAs from the sialyltransferase P-B3 gene suggests that they are very likely to be generated through alternative splicing and alternative promoter utilization mechanisms as observed for Galβ1, 4GlcNAc-α2,6-sialyltransferase (Galβ4GlcNAc-α6STRL) and Galβ1,3(4)GlcNAcα2,3-sialyltransferase (Galβ3(4) GlcNAc-α3STRL) (Weinstein, J. et al., J. Biol. Chem., 262, 17735–17743, 1987; and Wen, D. X. et al., J. Biol. Chem., 267, 21011–21019, 1992). This hypothesis is supported by the results of Southern hybridization, which showed the existence of a single copy gene for sialyltransferase P-B3.

A 1.3 kb DNA fragment encoding the full length sialyltransferase P-B3 was amplified using synthetic oligonucleotide primers (5'-ACGGC GCTCGAGCCAACCCGGAGAGCAGCG-3', and 5'-CGTTGC CTCGAGAGTCCTTGCAGTGGGACT-3', synthetic XhoI site underlined). The amplified DNA fragment was digested with XhoI and inserted into the XhoI site of the expression vector pcDSRα (Takebe, Y., Mol. Cell. Biol., 8, pp.466–472, 1988) to yield recombinant plasmid pcDB3ST. The insert of the plasmid was sequenced to confirm the absence of possible polymerase chain reaction errors.

COS-7 cells were transfected with 5 μg of the recombinant plasmid pcDB3ST using the DEAE-dextran method (McCutchan, J. H. and Pagano, J. S., J. Natl, Cancer Inst., 41, 351–357, 1968).

After 48 h of the transfection, the cultured cells (1×10$^7$) were harvested, washed with phosphate-buffered saline, and then resuspended in 2 ml of buffer comprising 20 mM MnCl$_2$ and 25 mM MES, pH 6.0. The cell suspension was centrifuged at 30,000×g for 30 min, the cell pellet was resuspended in 0.5 ml or 1% Triton X-100, 50 mM NaCl, 5 mM MnCl$_2$, 25 mM MES, pH 6.0, and then subjected to sonication. After centrifugation at 30,000×g for 30 min, the supernatant was concentrated 10-fold on Centricon 30 filters (Amicon), and then used for following assays.

The enzyme assays with glycoproteins, oligosaccharides and glycolipids as acceptors were performed in the presence of 0.1 M sodium cacodylate buffer (pH 6.0), 10 mM MgCl$_2$, 0.5% Triton CF54, 12 μM CMP-[$^{14}$C]NeuAc (1.5 kBq), 1 mg/ml acceptor substrate, and 1 μl of COS cell lysate (in a final volume of 10 μl ), with incubation at 37° C. for 1 hr. At the end of the incubation period, the reaction mixtures were subjected to SDS-PAGE for glycoproteins as acceptors, or were subjected to chromatography on HPTLC plates (Merck, Darmstadt, Germany) with a solvent system of ethanol/1-butanol/pyridine/acetic acid/water (100:10:10:3:30) for oligosaccharides and glycolipids as acceptors. Sialylated acceptors were quantified with a BAS2000 radio image analyzer (Fuji Photo Film, Japan).

Identifications of sialylated products were as follows. Reduced oligosaccharides were obtained from resialylated glycoproteins by β-elimination as described by Carlson (Carlson, D. M., J. Biol. Chem., 243, pp616–626, 1968). AsialoBSM was sialylated with CMP-[$^{14}$C]NeuAc in a pcDB3ST-transfected COS-7 cell lysate under the same conditions as above. The radiolabeled oligosaccharides released from fetuin were digested with NDV sialidase, and then subjected to thin layer chromatography for identification of the products without further purification. Oligosaccharides released from BSM were used as standards. AsialoBSM and asialofetuin were [$^{14}$C]-sialylated with the GalNAcα2,6-sialyltransferase P-B1 and Galβ1, 3GalNAcα2,3-sialyltransferase (Lee, Y. -C., et al., Eur J. Biochem., 216, pp. 377–385, 1993), respectively, and the oligosaccharides were prepared by β-elimination. The resulting [$^{14}$C]NeuAcα2,6GalNAc-ol, Galβ1,3([$^{14}$C] NeuAcα2,6)GalNAc-ol and [$^{14}$C]NeuAcα2,3Galβ1, 3GalNAc-ol were used as radio-labeled standards.

When fetuin was used as the acceptor, the acceptor was only sialylated by the lysate of COS-7 cells transfected with pcDB3ST. The expressed GalNAcα2,6-sialyltransferase P-B3 exhibited strong activity toward fetuin and asialofetuin, and weak activity toward asialoBSM, whereas no significant activity was observed toward BSM or other glycoproteins having only N-glycosidically linked oligosaccharides (e.g., α1-acid glycoprotein, ovomucoid, asialo-α1 acid glycoprotein and asialo-ovomucoid) (Table 2).

In addition, oligosacclharides or glycosphingolipids could not serve as acceptors for the GalNAcα2,6-sialyltransferase P-B3 of the present invention. [$^{14}$C]NeuAc residues incorporated into fetuin by the enzyme were resistant to treatment with N-glycanase or NDV sialidase. The radiolabelled oligosaccharides released from fetuin were co-migrated with Galβ1,3(NeuAcα2,6)GalNAc-ol after treatment with NDV sialidase. These results indicate that sialic acid residues were transferred through α2,6-linkages on GalNAc residues of O-glycosidically linked oligosaccharides of fetuin. Thus, the expressed enzyme apparently has GalNAcα2,6-sialyltransferase activity. However, asialoBSM was a much poorer acceptor than fetuin and asialofetuin for this GalNAcα2,6-sialyltransferase P-B3 of the present invention. The acceptor substrate specificity is different from that of the GalNAcα2,6-sialyltransferase P-B1 for which asialoBSM serves as a much better acceptor than asialofetuin.

To define the substrate specificity of the GalNAcα2,6-sialyltransferase P-B3 of the present invention, fetuin was sequentially treated with sialidase (*Vibrio cholerae*) and β-galactosidase (bovine testes), and the resulting asialofetuin and agalacto-asialofetuin were used as acceptors. The incorporation of NeuAc-residues for the sialidase-treated fetuin was increased 1.5-fold of that for native fetuin. Three O-glycosidically linked oligosaccharides are known to be contained in fetuin, two of which are NeuAcα2,3 Galβ1, 3GalNAc and the other is NeuAcα2,3Galβ1,3(NeuAcα2,6)-GalNAc (Spiro, R. G. and Bhoyroo, V. D., J. Biol. Chem., 249, 5704–5717, 1974). Accordingly, GalNAc residues in two of the three O-linked oligosaccharides can serve as acceptors in native fetuin, whereas those in all O-linked oligosaccharides in asialofetuin can be sialylated by the GalNAcα2,6-sialyltransferase P-B3 of the present invention.

Furthermore, agalacto-asialofetuin could not serve as an acceptor of the GalNAcα2,6-sialyltransferase P-B3 of the present invention, and only Galβ1,3([$^{14}$C]NeuAcα2,6) GalNAc-ol, but not [$^{14}$C]NeuAcα2,6-GalNAc-ol, was detected for the oligosaccharides released from asialoBSM incubated with the enzyme by β-elimination.

The characteristics of the GalNAcα2,6-sialyltransferase P-B3 of the present invention revealed by the above experiments can be summarized as follows:

(1-i) Fetuin and asialofetuin, which contain the O-glycosidically linked (NeuAcα2,3)Galβ1,3GalNAc sequence (Spiro, R. G. and Bhoyroo, V. D., J. Bio. Chem., 249, 5704–5717, 1974), served as good acceptors, but asialoBSM, in which only 5% of the total carbohydrate chains contain Galβ1,3GalNAc sequences (Tsuji, T. and Osawa, T., Carbohydr. Res., 151, 391–402, 1986), served as a much poorer acceptor; and (1-ii) the protein portion is essential for the activity of this sialyltransferase, since Galβ1,3GalNAcα1-Bz as well as asialoGM1 (Galβ1,3GalNAcβ1,4Galβ1,3Glcβ1-Cer) and GM1b (NeuAc α2,3Galβ1,3GalNAcβ1,4Galβ1,3Glcβ1-Cer) did not serve as acceptors.

(2) This sialyltransferase did not exhibit activity toward asialofetuin treated with β-galactosidase (agalactoasialofetuin).

(3) Only Galβ1,3([$^{14}$C]NeuAc-α2,6)GalNAc-ol was detected in the oligosaccharides released from [$^{14}$C] sialylated asialoBSM although about 60% of the carbohydrate chains of asialoBSM are GalNAc-O-Ser/Thr (Tsuji, T. and Osawa, T., Carbohydr. Res., 151, 391–402, 1986).

These results clearly suggest that the acceptor substrate of the enzyme of the present invention having catalytic activity, i.e., transfer of CMP-NeuAc with an α2,6-linkage onto a GalNAc residue O-linked to Thr/Ser of a glycoprotein, requires Galβ1,3 GalNAc sequence of O-glycoside linked oligosaccharide, whereas α2,3 linkage-sialic acid residues linked to galactose residues are not essential for the activity. Therefore, the enzyme P-B3 first cloned by the present invention is a novel type of GalNAcα2,6-sialyltransferase. The primary sequence of GalNAcα2,6-sialyltransferase P-B3 from the 45 amino acid regions at the molecular center (sialylmotif L) to the COOH-terminal (residues: 180–404) exhibits high sequence homology to that of GalNAcα2,6-sialyltransferase P-B1(FIGS. 4A and 4B: the identity is 48%). The conserved regions unique to these GalNAcα2,6-sialyltransferases may be correlated with their enzymatic function of transferring sialic acid to the GalNAc-moiety via an α2,6-linkage.

TABLE 2

Acceptor substrate specificity of GalNAcα 2,6-sialyltransferase P-B3 of the invention

| Acceptor | Specificity pmol/h/μ 1 enzyme fraction |
|---|---|
| Fetuin | 28 |
| Asialofetuin | 35 |
| BSM | 0.5 |
| AsialoBSM | 5.2 |
| α 1-Acid glycoprotein | 0 |
| Asialo- α 1-acid glycoprotein | 1.2 |
| Ovomucoid | 0 |
| Asialo-ovomucoid | 1.0 |
| Gal β 1,3GalNAc α 1-Bz | 0 |
| GalNAc α 1-Bz | 0 |
| GalNAc-SerNAc | 0 |
| AsialoGM1 | 0 |
| GM1b | 0 |
| Ganglioside Mixture | 0 |

0 indicates less than 0.5 pmol/h.

The regents, samples and the like used in the above preparation example (C) were as follows. Fetuin, asialofetuin, bovine submaxillary mucin, α1-acid glycoprotein, galactoseβ1,4-N-acetylgalactosamine, CMP-NeuAc, Galβ1,3GalNAcα1-Bz, GalNAcα1-Bz and Triton CF-54 were obtained from Sigma (St. Louis, USA). CMP-[$^{14}$C]NeuAc (11 GBq/mmole) was obtained from Amersham (U.K.). 2-Acetamide and 2-deoxygalactosylα N-acetylserine (GalNAc-SerNAc) was synthesized according to Grundler and Schmidt (Grundler G., and Schmidt R. R., Liebigs Ann. Chem., 1984, 1826–1847, 1984). NDV-sialidase and sialidase from *Vibrio cholerae* were purchased from Oxford Glycosystems (U.K.) and Boehringer Mannheim (Germany), respectively. p-Galactosidase from bovine testes was obtained from Boehringer Mannheim (Germany). Synthetic primers were synthesized with the Applied Biosystem 394 DNA synthesizer. Restriction endonucleases were obtained from Takara (Japan).

(D) Purification of Sialyltransferase Expressed in Microorganisms Plasmid Construction An initiation codon and cloning sites were attached by PCR to mouse Galβ1,4GlcNAcα2,6-Sialyltransferase cDNA (Hamamoto, T. et al., Bioorg. Medicin. Chem., 1, 141–145, 1993). 5'-TGGCATATGGGGAGCG ACTATGAGGCTCT-3'containing an NdeI site was used as a sense primer and 5'-ATGAGGATCCCTGGCTCAACAGCG-3' containing a BamHI site as an antisense primer. The resulting PCR fragment (1152 bp) contained the initiation codon and a region coding for a polypeptide from the 29th amino acid residue to the C-terminal end of the enzyme, and lacked the cytosolic and transmembrane domains. The fragment was incorporated into expression vector pET3b (Studier, F. W. et al., Method. Enzymol., 185, 60–89, 1990) at the NdeI-BamHI site (located downstream of the T7 promoter). The resulting recombinant vector was named as pET3-MBS. The nucleotide sequence of the PCR fragment is shown as the SEQ ID No.4 in the sequence listings.

Enzyme Expression

*E. coli* JM109(DE3) cells transfected with the vector pET3-MBS were cultured in 100 ml LB medium supplemented with 100 μg/ml ampicillin at 37° C. When the optical density at 600 nm reached 0.2–0.4, production of the recombinant protein was initiated with induction of T7 RNA polymerase by the addition of 2 mM IPTG (isopropylβ-D-thiogalatopyranoside). The recombinant enzyme, lacking the cytosolic and the transmembrane domain, was accumulated in the form of insoluble inclusion bodies in the cells. The growth rate of the JM109(DE3) cells transfected with pET3-MBS was the same as that of the non-transfected JM109(DE3) cells both on agar plates and in liquid culture. After 2 h cultivation, the cells were harvested (ca. 1 g wet weight), suspended in 10 ml of 20 mM Tris-HCl (pH 8.0), and then treated with lysozyme (0.1 mg/ml) and DNase I (0.01 mg/ml) for 30 min. Triton X-100 was added to a final concentration of 1%, and insoluble fraction was collected by centrifugation at 12,000×g for 15 min at 4° C. The precipitate was suspended in 3 ml of 10 mM Tris-HCl (pH 7.4) and stored at −30° C. before use.

Solubilization and Renaturation

To 0.5 ml of the above suspension, 0.48 g solid urea, 60 μl of 5 M NaCl, 20 μl of 1 M Tris-HCl (pH 7.4) and water were added to final volume of 1 ml (final concentration: 8 M urea, 0.3 M NaCl; 20 mM Tris-HCl, pH 7.4). The precipitate was extracted for 30 min at 10° C., followed by centrifugation at 12,000×g for 15 min. Most of the extracted protein had the molecular mass of 42 k dalton. Where 5.7 M urea buffer was used for the extraction, 80% of the enzyme was recovered.

The 0.1 ml aliquots of extract containing 8 M urea were diluted with each 1.9 ml of a renaturation composition (standard composition: 2 M urea, 0.5 M NaCl, 10 mM lactose, 0.5 mM EDTA, and 20 mM MOPS-NaOH, pH 7.0) to a final protein concentration of about 0.02 mg/ml. The solution was left at 40° C. for 1.2 h, and then diluted again with an equal volume of the renaturation composition, thereby reducing the urea concentration to half (approximately 1.2 M), and then the mixture was left at 40° C. for additional 48 h. Then, sialyltransferase activity was measured to analyze the effects of the components of the renaturation composition at this point (Table 3). The resulting enzymes were further dialyzed against the renaturation composition to remove residual urea and the reducing agents over 48 h at 4° C. The samples were concentrated approximately 20 times with Centricon-30 (Amicon).

Sialyltransferase Assay

The activity of the sialyltransferase was measured with 50 μM CMP-[$^{14}$C]NeuAc (0.9 Bq/pmole) as a donor substrate, and 5 mM Galβ1,4GlcNAc (N-acetyllactosamine) as an acceptor substrate. Reaction mixture was added with 1 mg/ml bovine serum albumin, 1 μl of the enzyme solution, and 50 mM sodium cacodylate (pH 6.0) to a total volume of 10 μl and incubation was continued at 37° C. for 1 h. Then, the samples were applied to silica gel60 HPTLC plate (Merck Germany) and developed with ethanol/pyridine/n-butanol/acetic acid/water (100:10:10:3:30) as a developing solvent. The radioactivity transferred on each plate was determined with a radio image analyzer BAS2000 (Fuji Photo Film, Japan, Thee, Y. -C. et al., Eur. J. Biochem., 216, 377–385, 1993). One unit of enzymatic activity was defined as an amount catalyzing 1 μ mole of sialic acid transfer per minute. The acceptor preference as to oligosaccharide branches was examined using a N-acetyllactosamine type biantennary pyridylamino-oligosacchiaride as an acceptor substrate and analyzed fluorophotometrically by HPTC.

When the 8 M urea extract was dialyzed without dilution at 4° C., almost no activity of the enzyme precipitated at urea concentration of less than 0.5 M was recovered. The results of the optimum dilution conditions at 48 h after the second dilution are shown in Table 3 set out below. In the table, the standard renaturation composition was comprised of: 2 M urea, 20 mM Tris-HCl, 0.3 M NaCl, 20 mM lactose, and 0.5 mM EDTA (pH 7.4), and as to other compositions, deviations from the standard composition are indicated.

TABLE 3

The effects of various conditions on renaturation of Gal β 1,4GalNAcα 2,6-sialyltransferase

| Renaturation conditions | Relative activity compared\to standard |
|---|---|
| Standard composition | 1 |
| pH 9.5, Tris-HCl 20 mM | 0* |
| pH 8.0, Tris-HCl 20 mM | 0.6 |
| pH 7.0, MOPS-NaOH 20 mM | 2.5 |
| pH 6.0, MES-NaOH 20 mM | 1.5 |
| 0.5 M NaCl | 2 |
| 0.1 M NaCl | 0.2 |
| 0.01 M NaCl | 0 |
| 0 mM lactose | 0.5 |
| 1 M urea | 1.5 |
| 0 M urea | 0.6 |

*A value of 0 indicates less than 5% of the control.

The maximum renaturation was observed with 0.5 M NaCl (pH 7.0) in the standard composition, and these compositions were used in further experiments. After three independent renaturation experiments were carried out under this condition, total recovered activities were 0.4–0.8 mU/0.1 ml extract. The enzymes at this stage of renaturation showed high Km values for CMP-NeuAc and N acetyliactosamine, 0.14 mM and 20 mM, respectively. Under the conditions tested, reducing agents (DTT and β-mercaptoethanol) inhibited the enzyme activity, which may due to the carryover of urea at the concentration of 0.1 M in the assay mixture. In addition, very little activity was observed at 12 h after the second dilution, which apparently indicates that a refolding process of the polypeptide is very slow at the test temperature. Almost the same activity, as that in the process without the use of the reducing reagents, was obtained by the following process: the 8 M urea extract was diluted with 20 volumes of the renaturation composition containing 2 M urea, 20 mM MOPS-NaOH, pH 7.0, 0.5 M NaCl, 20 mM lactose, and 0.5 mM EDTA in the presence of 1 μM or 1 mM reducing regents, and then samples were left at 4° C. for 12 h and diluted to reduce the urea concentration to half, and the residual urea and reducing reagents were removed by dialysis. The results are shown in Table 4.

TABLE 4

| Reducing regent | Specific activity (mU/mg) |
|---|---|
| None | 7 |
| 1 μM DTT | 6 |
| 1 mM DTT | 12 |

The substrate specificity of renatured mouse Galβ1, 4GlcNAcα2,6-sialyltransferase was assayed using each 2 mg/ml of substrates. The products were analyzed by HPTLC. HPTLC was performed using ethanol/pyridine/n-butanol/acetic acid/water (100:10:10:3:30) as a developing solvent when oligosaccharides and glycoproteins were used as acceptors, and chloroform:methanol:0.5% $CaCl_2$ (55:45:8) as a developing solvent when glycolipids were used as acceptors. The substrate specificity and kinetic parameters of the renatured enzymes were similar to those of the enzyme obtained from rat liver.

The results are shown in Table 5 and Table 6.

TABLE 5

| | Relative Activity to Gal β 1,4GlcNAc | |
|---|---|---|
| Substrate | Renatured mouse Gal β 1,4GlcNAc α 2,6-sialyltransferase | Rat liver Gal β 1,4GlcNAc α a2, 6-sialyltransferase |
| Fetuin | 0.25 | 0* |
| Asialofetuin | 1.5 | 0.97 |
| α 1 acid glycoprotein | 0.1 | 0.1 |
| Asialo-α 1 acid glycoprotein | 2.1 | 1 |
| Bovine submaxillary mucin | 0 | 0 |
| Bovine submaxillary asialo-mucin | 0 | 0 |
| Lacto N-tetraose | 0 | 0 |
| Galβ 1,4GlcNAc | 1 | 1 |
| Galβ 1,3GlcNAc | 0 | 0 |
| GalNAc β 1,4Gal | 0 | 0 |
| Gal β 1,4Glc | 0 | 0 |
| Gal | 0 | 0 |

*A value of 0 indicates less than 2% of the control.

TABLE 6

| | Km (mM) | |
|---|---|---|
| Substrate | Renatured mouse Gal β 1,4GlcNAc α 2, 6-sialyltransferase | Rat liver Gal β 1,4GlcNAc α a2, 6-sialyltransferase |
| CMP-NeuAc* | 0.08 | 0.04 |
| N-acetyllactosamine | 6.5 | 5 |
| Asialo-orosomucoid** | 0.4 | 0.2 |

*Measured with N-acetyllactosamine as the acceptor.
**Concentration expressed as terminal galactose residues.

Galβ1,4GlcNAcα2,6-sialyltransferase is capable of recognizing the different branches of biantennary glycopeptides of the N-acetyllactosamine type (Joziasse, D. H. et al., J. Biol. Chem., 260, 714–719, 1985; and Van den Eijnden D. H. et al., Biochem. Biophys. Res. Comm., 92, 839–845, 1980). A desialylated biantennary PA-oligosaccharide was sialylated by the enzyme renatured according to the method of the present invention and then analyzed with HPLC. The assays were performed using 10 pmoles of acceptor substrates and 0.1 mM CMP-NeuAc in a final volume of 5 μl. The reaction mixtures were incubated at 37° C. for 1 h, and the reaction was stopped by the addition of 90 μl of cold water. To identify sialylated pyridylamino oligosaccharides, each reaction mixture was subjected to HPLC analyses equipped with a reversed-phase column (Shimpack CLC-ODS, 0.6 cm×15 cm, Shimazu, Japan). The column was equilibrated with mixture of 70% solvent A (10 mM sodium phosphate, pH 3.8) and 30% solvent B (0.5% n-butanol, 10 mM sodium phosphate, pH 3.8), and eluted at the flow rate of 1 ml/min with a linear gradient of solvent B to 60% over 30 min at 55° C. Pyridylamino oligosaccharides were detected fluorophotometrically (excitation at 320 nm and emission at 400 nm), and the results indicated that the renatured enzyme showed higher preference for galactose residues on Manα1,3 branches rather than for galactose residues on Manα1,6 branches like the native enzyme.

By competely remove urea, the renatured enzyme restored its resistance to reducing agents. In addition, more than 10 times activation was recovered by renaturing with the addition of divalent cations. While not bound by any specific theory, where dialysis is carried out for a prolonged period of time against a dialysis buffer containing 0.5 mM EDTA in the presence of urea, divalent cations, which are tightly bound to the enzyme to maintain the proper conformation of the enzyme, may be lost. Where the enzyme was renatured in the renaturation composition containing 1.2 M urea, the addition of divalent cations increased the activity. The results obtained are shown in Table 7. In the table, the activities are shown as relative values to that obtained by no addition of reagents. The specific activity of the renatured enzyme was 0.15 U/mg protein when measured with 5 mM $MnCl_2$, which is about 2% of that of the enzyme obtained from rat liver (Weinstein, J. et al., J. Biol. Chem., 257, pp.13835–13844, 1982). The overall recovery of the enzyme was 0.1 U/100 ml culture medium.

TABLE 7

| Reagent | | Renatured mouse Gal β 1,4GlcNAc α 2, 6-sialyltransferase | Rat liver Gal β 1,4GlcNAc α 2, 6-sialyltransferase |
|---|---|---|---|
| Reducing agent | | | |
| DTT | (1 mM) | 1.0 | 0.9 |
|  | (1 μM) | 1.1 | 1.2 |
| Mercapto-ethanol | (1 mM) | 1.1 | 1.1 |
|  | (1 μM) | 1.0 | 1.1 |
| Detergent | | | |
| Triton x-100 | (1%) | 1.5 | 0.8 |
|  | (0.5%) | 1.4 | 1.4 |
|  | (0.1%) | 1.3 | 1.3 |
| Divalent cations | | | |
| MgCl$_2$ | (5 mM) | 11 | 1.0 |
| MnCl$_2$ | (5 mM) | 13 | 1.1 |
| EDTA | (5 mM) | 1.7 | 0.9 |

The method of the present invention was specifically explained above referring to the examples relating to the Galβ1,4GlcNAcα2,6-sialyltransferase. However, the method of the present invention is not limited to these examples. As described above, unlike other glycosyltransferases, sialyltransferases share highly conserved regions (sialylmotif, Livingston, B. D. and Paulson, J. C., J. Biol. Chem.,268, 11504–11507, 1993), and all of the sialyltransferases are considered to have similar higher-order structures (Drickamer, K., Glycobiology, 3, 2–3, 1993). Therefore, it is readily understood by those skilled in the art that the renaturation procedure disclosed in the above examples for Galβ1,4GlcNAcα2,6-sialyltransferase can be applied to renaturations of other sialyltransferases to achieve the same advantageous effects. Furthermore, those skilled in the art will be able to choose optimum renaturing conditions, not only for Galβ1,4GlcNAcα2,6-sialyltransferase but for other sialyltransferases, by modifying or altering the processes disclosed in the specification.

The regents and samples used in the above example (D) were as follows. Rat liver Galβ1,4GlcNAcα2,6-sialyltransferase, fetuin, asialo-fetuin, bovine submaxillary mucin, α1-acid glycoprotein, galactoseβ1,3-N-acetylgalactosamine, lacto N-tetraose and N-acetyllactosamine were obtained from Sigma (St. Louis, USA). Urea was purchased from Wako Pure Chemicals (Osaka, Japan) and a solution was prepared just before use. CMP-[$^{14}$C]NeuAc (11 GBq/mmole) was obtained from Amersham (U.K). Bovine submaxillary asialo-mucin and asialo-α1-acid glycoprotein were obtained by mild acid treatment of corresponding glycoproteins. N-acetylgalactosamine e β1,4-galactose was a kind gift from Dr. Kajimoto (The institute of Physical and Chemical Research, RIKEN, Wako-shi, Saitama-ken, Japan). Pyridylamino oligosaccharides (PA-sugar 001, 021, 022 and 023) were obtained from Takara (Kyoto, Japan). Protein concentrations were determined with a BCA protein assay kit (Pierce) using bovine serum albumin as the standard. Dialysis tubing (20/32) was from Viskase.

INDUSTRIAL APPLICABILITY

The novel GalNAcα2,6-sialyltransferases P-B1 and P-B3, and proteins which contain a polypeptide part as being the active domain of said enzymes and are released extracellularly provided by the present invention are useful as, for example, reagents for introducing human type sugar-chain to proteins and medicament for treating hereditary diseases lacking human-specific sugar chains. In addition, they can be used as drugs for inhibiting tumor metastases, preventing viral infection, and controlling inflammatory reaction. Furthermore, the method of the present invention is useful when a large quantity of a sialyltransferase is expressed in microorganisms, since it enables a mass recovery of the enzyme with highly restored activity from aggregate or precipitate inside the cells.

What is claimed is:

1. An isolated DNA comprising a nucleic acid sequence encoding at least an active domain of a GalNAcα2,6-sialyltransferase.

2. The DNA according to claim 1, wherein the nucleic acid sequence encodes GalNAcα2,6-sialyltransferase P-B1 having the amino acid sequence set forth in SEQ ID NO.5.

3. The DNA according to claim 1, wherein the nucleic acid sequence encodes GalNAcα2,6-sialyltransferase P-B1 and is nucleotide 1 to 1698 of SEQ ID NO. 1.

4. The DNA according to claim 1, wherein the nucleic acid sequence encodes an active domain having an amino acid sequence of amino acid 233 to amino acid 566 of SEQ ID NO.5.

5. The DNA according to claim 1, wherein the nucleic acid sequence encodes an active domain and is nucleotide 697 to nucleotide 1698 of SEQ ID NO. 1.

6. The DNA according to claim 1, wherein the nucleic acid sequence encodes GalNAcα2,6-sialyltransferase P-B3 having the amino acid sequence set forth in SEQ ID NO.7.

7. The DNA according to claim 1, wherein the nucleic acid sequence encodes GalNAcα2,6-sialyltransferase P-B3 and is nucleotide 1 to nucleotide 1212 of SEQ ID NO. 3.

8. A recombinant vector comprising the DNA according to any one of claims 1–7.

9. The recombinant vector according to claim 8, which is plasmid CEB-3034, plasmid CEB3-T20 or plasmid pcDB3ST.

10. A transformant containing a recombinant vector according to claim 8.

11. A transformant containing a recombinant vector according to claim 9.

12. A DNA comprising a nucleic acid sequence encoding an extracellularly releasable recombinant fusion protein, said fusion protein comprising an active domain of a GalNAcα2,6-sialyltransferase and a signal peptide.

13. The DNA according to claim 12, wherein the GalNAcα2,6-sialyltransferase is GalNAcα2,6-sialyltransferase P-B1 having the amino acid sequence set forth in SEQ ID NO.5.

14. The DNA according to claim 12, wherein the GalNAcα2,6-sialyltransferase is encoded by nucleotide 1 to nucleotide 1698 of SEQ ID NO. 1.

15. The DNA according to claim 12, wherein the active domain comprises amino acid 233 to amino acid 566 set forth in SEQ ID NO.5.

16. The DNA according to claim 12, wherein the active domain is encoded by nucleotide 697 to nucleotide 1698 set forth in SEQ ID NO. 1.

17. The DNA according to claim 12, wherein the GalNAcα2,6-sialyltransferase is GalNAcα2,6-sialyltransferase P-B3 having the amino acid sequence set forth in SEQ ID NO.7.

18. The DNA according to claim 12, wherein the GalNAcα2,6-sialyltransferase is encoded by nucleotide 1 to nucleotide 1212 of SEQ ID NO. 3.

19. The DNA according to claim 12, which encodes the amino acid sequence set forth in SEQ ID NO.6.

20. The DNA according to claim 12, which has the nucleic acid sequence of nucleotide 1 to nucleotide 1065 of SEQ ID NO. 2.

21. The DNA according to claim 12, wherein said signal peptide is located on the N-terminal side of the active domain and replaces the hydrophobic segment of the GalNAcα2,6-sialyltransferase.

22. A recombinant vector, which comprises the DNA according to any one of claims 12–21.

23. The recombinant vector according to claim 22, which is plasmid pcDSB-690.

24. A transformant containing a recombinant vector according to claim 22.

25. A transformant containing a recombinant vector according to claim 23.

26. A process for preparing an extracellularly releasable protein catalyzing GalNACα2,6-sialic acid transfer, which comprises culturing a transformant according to claim 24, and recovering said protein from the culture.

27. A process for preparing a sialyltransferase which comprises the steps of:

(a) expressing a sialyltransferase in a microorganism;

(b) extracting the sialyltransferase using 5 to 9 M urea from proteinic aggregate or precipitate that contains the enzyme and is accumulated inside the microorganism;

(c) diluting the extract obtained by the step (b) with a renaturation composition to obtain a primary dilution containing 1 to 4 M urea;

(d) diluting the primary dilution obtained by the step (c) with a renaturation composition to obtain a secondary dilution containing 0.5 to 2 M urea; and (e) removing urea from the secondary dilution obtained by the step (d) by dialysis to afford a renatured sialyltransferase.

28. The process according to claim 27, wherein the renaturation composition used in the step (c) comprises 1 to 2 M urea, 20 mM MOPS-NaOH, 0.5 M NaCl, 20 mM lactose, and 0.5 mM EDTA (pH 7.0); and the renaturation composition used in the step (d) comprises 20 mM MOPS-NaOH, 0.5 M NaCl, 20 mM lactose, and 0.5 mM EDTA (pH 7.0).

29. A process for preparing a sialyltransferase which comprises the steps of:

(a) expressing a sialyltransferase in a microorganism;

(b) extracting the sialyltransferase using 8 M urea from proteinic aggregate or precipitate that contains the enzyme and is accumulated inside the microorganism;

(c) diluting the extract obtained by the step (b) with a renaturation composition, followed by standing the dilution for at least 12 hours at 4° C. to obtain a primary dilution containing 2 to 3 M urea;

(d) diluting the primary dilution obtained by the step (c) with a renaturation composition, followed by standing the dilution for at least 48 hours to obtain a secondary dilution containing 1 to 2 M urea; and (e) removing urea from the secondary dilution obtained by the step (d) by dialysis in the presence of one or more divalent cations to afford a renatured sialyltransferase.

30. The process according to claim 29, wherein the renaturation composition used in the step (c) comprises 1 to 2 M urea, 20 mM MOPS-NaOH, 0.5 M NaCl, 20 mM lactose, and 0.5 mM EDTA (pH 7.0); and the renaturation composition used in the step (d) comprises 20 mM MOPS-NaOH, 0.5 M NaCl, 20 mM lactose, and 0.5 mM EDTA (pH 7.0).

31. A process according to claim 29, wherein the sialyltransferase is GalNAcα2,6-sialyltransferase or Galβ1,4GlcNAcα2,6-sialyltransferase.

* * * * *

SEQUENCE LISTING (1) GENERAL INFORMATION:

(iii) NUMBER OF SEQUENCES:  8

(2) INFORMATION FOR SEQ ID NO:1:

(i) SEQUENCE CHARACTERISTICS:
        (A) LENGTH: 2671
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:1:

```
ATG GGG TTT TTA ATC AGA AGG CTT CCT AAA GAT TCC AGA ATA TTC         45
MET Gly Phe Leu Ile Arg Arg Leu Pro Lys Asp Ser Arg Ile Phe
 1               5                  10                  15

CGT TGG CTC CTT ATT TTA ACA GTC TTT TCC TTC ATC ATT ACT AGT         90
Arg Trp Leu Leu Ile Leu Thr Val Phe Ser Phe Ile Ile Thr Ser
                20                  25                  30
```

```
TTT AGC GCC TTG TTT GGC ATG GAG AAA AGC ATT TTC AGG CAG CTC          135
Phe Ser Ala Leu Phe Gly MET Glu Lys Ser Ile Phe Arg Gln Leu
                 35                  40                  45

AAG ATT TAC CAA AGC ATT GCA CAT ATG CTA CAA GTG GAC ACC CAA          180
Lys Ile Tyr Gln Ser Ile Ala His MET Leu Gln Val Asp Thr Gln
                 50                  55                  60

GAT CAG CAA GGT TCA AAC TAT TCT GCT AAT GGG AGA ATT TCA AAG          225
Asp Gln Gln Gly Ser Asn Tyr Ser Ala Asn Gly Arg Ile Ser Lys
                 65                  70                  75

GTT GGT TTG GAG AGA GAC ATT GCA TGG CTC GAA CTG AAT ACT GCT          270
Val Gly Leu Glu Arg Asp Ile Ala Trp Leu Glu Leu Asn Thr Ala
                 80                  85                  90

GTG AGT ACA CCA AGT GGG GAA GGG AAG GAA GAG CAG AAG AAA ACA          315
Val Ser Thr Pro Ser Gly Glu Gly Lys Glu Glu Gln Lys Lys Thr
                 95                 100                 105

GTG AAA CCA GTT GCC AAG GTG GAA GAA GCC AAG GAG AAA GTG ACT          360
Val Lys Pro Val Ala Lys Val Glu Glu Ala Lys Glu Lys Val Thr
                110                 115                 120

GTG AAA CCA TTC CCT GAG GTG ATG GGG ATC ACA AAT ACA ACA GCA          405
Val Lys Pro Phe Pro Glu Val MET Gly Ile Thr Asn Thr Thr Ala
                125                 130                 135

TCA ACA GCC TCT GTG GTG GAG AGA ACA AAG GAG AAA ACA ACA GCG          450
Ser Thr Ala Ser Val Val Glu Arg Thr Lys Glu Lys Thr Thr Ala
                140                 145                 150

AGA CCA GTT CCA GGG GTG GGG GAA GCT GAT GGG AAG AGA ACA ACG          495
Arg Pro Val Pro Gly Val Gly Glu Ala Asp Gly Lys Arg Thr Thr
                155                 160                 165

ATA GCA CTT CCC AGC ATG AAG GAA GAC AAA GAG AAG GCG ACT GTG          540
Ile Ala Leu Pro Ser MET Lys Glu Asp Lys Glu Lys Ala Thr Val
                170                 175                 180

AAA CCA TCC TTT GGG ATG AAG GTA GCT CAT GCA AAC AGC ACA TCC          585
Lys Pro Ser Phe Gly MET Lys Val Ala His Ala Asn Ser Thr Ser
                185                 190                 195

AAA GAT AAA CCA AAG GCA GAA GAG CCT CCT GCA TCA GTG AAA GCC          630
Lys Asp Lys Pro Lys Ala Glu Glu Pro Pro Ala Ser Val Lys Ala
                200                 205                 210

ATA AGA CCT GTG ACT CAG GCT GCC ACA GTG ACA GAG AAG AAG AAA          675
Ile Arg Pro Val Thr Gln Ala Ala Thr Val Thr Glu Lys Lys Lys
                215                 220                 225

CTG AGG GCT GCT GAC TTC AAG ACT GAG CCA CAG TGG GAT TTT GAT          720
Leu Arg Ala Ala Asp Phe Lys Thr Glu Pro Gln Trp Asp Phe Asp
                230                 235                 240

GAT GAG TAC ATA CTG GAT AGC TCA TCT CCA GTA TCG ACC TGC TCT          765
Asp Glu Tyr Ile Leu Asp Ser Ser Ser Pro Val Ser Thr Cys Ser
                245                 250                 255

GAA TCA GTG AGA GCC AAG GCT GCC AAG TCT GAC TGG CTG CGA GAT          810
Glu Ser Val Arg Ala Lys Ala Ala Lys Ser Asp Trp Leu Arg Asp
                260                 265                 270

CTT TTC CTG CCG AAC ATC ACA CTC TTC ATA GAC AAG AGT TAC TTC          855
Leu Phe Leu Pro Asn Ile Thr Leu Phe Ile Asp Lys Ser Tyr Phe
                275                 280                 285

AAT GTC AGT GAG TGG GAC CGC CTG GAG CAT TTT GCA CCT CCC TAT          900
Asn Val Ser Glu Trp Asp Arg Leu Glu His Phe Ala Pro Pro Tyr
                290                 295                 300

GGC TTC ATG GAG CTG AAT TAC TCA CTG GTA GAA GAA GTC ATG TCA          945
Gly Phe MET Glu Leu Asn Tyr Ser Leu Val Glu Glu Val MET Ser
                305                 310                 315

CGG CTG CCT CCA AAT CCC CAC CAG CAG CTG CTC CTG GCC AAC AGT          990
Arg Leu Pro Pro Asn Pro His Gln Gln Leu Leu Leu Ala Asn Ser
                320                 325                 330
```

```
AGC AGC AAC GTG TCA ACG TGC ATC AGC TGT GCT GTT GTG GGG AAT      1035
Ser Ser Asn Val Ser Thr Cys Ile Ser Cys Ala Val Val Gly Asn
                335                 340                 345

GGA GGG ATA TTG AAT AAC TCT GGA ATG GGC CAG GAG ATT GAC TCC      1080
Gly Gly Ile Leu Asn Asn Ser Gly MET Gly Gln Glu Ile Asp Ser
                350                 355                 360

CAT GAC TAT GTG TTC CGG GTG AGC GGG GCT GTA ATC AAA GGT TAC      1125
His Asp Tyr Val Phe Arg Val Ser Gly Ala Val Ile Lys Gly Tyr
                365                 370                 375

GAA AAG GAT GTG GGA ACA AAA ACC TCC TTC TAC GGA TTC ACA GCG      1170
Glu Lys Asp Val Gly Thr Lys Thr Ser Phe Tyr Gly Phe Thr Ala
                380                 385                 390

TAC TCC CTG GTG TCC TCT CTC CAG AAC TTG GGA CAC AAA GGG TTC      1215
Tyr Ser Leu Val Ser Ser Leu Gln Asn Leu Gly His Lys Gly Phe
                395                 400                 405

AAG AAG ATC CCA CAG GGG AAG CAT ATC AGA TAC ATT CAC TTC CTG      1260
Lys Lys Ile Pro Gln Gly Lys His Ile Arg Tyr Ile His Phe Leu
                410                 415                 420

GAG GCA GTT AGA GAC TAT GAG TGG CTG AAG GCT CTT CTG TTG GAC      1305
Glu Ala Val Arg Asp Tyr Glu Trp Leu Lys Ala Leu Leu Leu Asp
                425                 430                 435

AAG GAT ATC AGG AAA GGA TTC CTG AAC TAC TAT GGG CGA AGG CCC      1350
Lys Asp Ile Arg Lys Gly Phe Leu Asn Tyr Tyr Gly Arg Arg Pro
                440                 445                 450

CGG GAG AGA TTC GAT GAA GAT TTC ACA ATG AAT AAG TAC CTG GTA      1395
Arg Glu Arg Phe Asp Glu Asp Phe Thr MET Asn Lys Tyr Leu Val
                455                 460                 465

GCT CAC CCT GAT TTC CTC AGA TAC TTG AAA AAC AGG TTC TTA AAA      1440
Ala His Pro Asp Phe Leu Arg Tyr Leu Lys Asn Arg Phe Leu Lys
                470                 475                 480

TCT AAA AAT CTG CAA AAG CCC TAC TGG CGG CTG TAC AGA CCC ACA      1485
Ser Lys Asn Leu Gln Lys Pro Tyr Trp Arg Leu Tyr Arg Pro Thr
                485                 490                 495

ACA GGA GCC CTC CTG CTG CTG ACT GCC CTG CAT CTC TGT GAC CGG      1530
Thr Gly Ala Leu Leu Leu Leu Thr Ala Leu His Leu Cys Asp Arg
                500                 505                 510

GTG AGT GCC TAT GGC TAC ATC ACA GAA GGT CAC CAG AAG TAC TCG      1575
Val Ser Ala Tyr Gly Tyr Ile Thr Glu Gly His Gln Lys Tyr Ser
                515                 520                 525

GAT CAC TAC TAT GAC AAG GAG TGG AAA CGC CTG GTC TTC TAC GTT      1620
Asp His Tyr Tyr Asp Lys Glu Trp Lys Arg Leu Val Phe Tyr Val
                530                 535                 540

AAC CAT GAC TTC AAC TTG GAG AAG CAG GTG TGG AAA AGG CTT CAT      1665
Asn His Asp Phe Asn Leu Glu Lys Gln Val Trp Lys Arg Leu His
                545                 550                 555

GAT GAG AAC ATC ATG AAG CTC TAC CAG AGA TCC TGA CAG TGT GCC      1710
Asp Glu Asn Ile MET Lys Leu Tyr Gln Arg Ser
                560                 565

GAGGGCCATT GCCTGGGAAA TCTCAACAGC ACCTCATGGG AACAGAAGA            1760

GGACCTCGGA AGCCAGGGTT AGCTCTGGAC TTCCAGGCCC AGCTTCAGCT           1810

CCACAGAGAT ATTTCCCTCC TTTGATATCT TTATTTTCTC ACAACACTTC           1860

CTAAAATGTG CATATTCTAC AGACCAAGCG AACAGTAGGG AAAAGTGCCT           1910

CCAAACAAGG TCCCATCTGA CTTGTGGACG GTTGTAGGCT CTGGTACTGG           1960

GAAAGAGGAA TCCGGGATGA ATCCGAATAG CAGATGTTCC AGTGCCCATT           2010

ATCTTAATCA GGTTCTCCCT CTGCAAGGAG ATGCTCTTGG GGCTGGGGCT           2060
```

-continued

| | |
|---|---|
| AGTTTTGCTC TAGGTGGGTT CTCTCTGTGA GTAGTGCTTG TTATGGAGCT | 2110 |
| GGGTGTTTTG GGTAAGCAGT GGATAGAATG GAGACACACA CAATCCTGTC | 2160 |
| TCAAGAGGAT GATTTGTGTC CTGGAGGTGC TGCTGTCACT CTGCTCACTG | 2210 |
| CAGGCATAAG GACCCTTCCA ATGAACTCAA TCCCAATGTG ACTTTGCTGT | 2260 |
| GACACCTCCT GGGGAGCACT GTGATGTCGG TGCCCAGCCT GCTGCCCTTG | 2310 |
| GCCTAGTTCA CCATCAGCAC AAGGGAAGGG GAGAGCCCTC CGTAGTGCAG | 2360 |
| CAGAATGCTG GACATTGTAC CTCTTGCTGT GGGTTCCCCT GGCTGCAGAC | 2410 |
| TACGTGTAGT GAGTCTGATG AAGAAGCTGG TGCTTGGCTG TGCCAGGAGC | 2460 |
| ATGGTGCTTC CTCTTCTACC AGGAGAAATG AGAATTCTCA ATGTCCATGG | 2510 |
| ATGGATGCTG TCTGTCCTTG CTGCTGGCTG GAGTGCCTGC CTACATTGTC | 2560 |
| CTGAGAAAAG CACTGTTACA GCCAGTAAGC CTTTGGAGTA TTGGCCTTCT | 2610 |
| GAGTGGGCTT TTGCAAACAA AATAAACGGC ACTGCTTTCC CCCAAGCTGA | 2660 |
| AAAAAAAAAA A | 2671 |

(2) INFORMATION FOR SEQ ID NO:2:

(i) SEQUENCE CHARACTERISTICS:
        (A) LENGTH: 1206
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:2:

| | |
|---|---|
| ATG AAA TTC AGC TGG GTC ATG TTC TTC CTG ATG GCA GTG GTT ACA<br>MET Lys Phe Ser Trp Val MET Phe Phe Leu MET Ala Val Val Thr<br>1                 5                       10                  15 | 45 |
| GGG GTC AAT TCA GAA TTC ACT GAG CCA CAG TGG GAT TTT GAT GAT<br>Gly Val Asn Ser Glu Phe Thr Glu Pro Gln Trp Asp Phe Asp Asp<br>                20                       25                  30 | 90 |
| GAG TAC ATA CTG GAT AGC TCA TCT CCA GTA TCG ACC TGC TCT GAA<br>Glu Tyr Ile Leu Asp Ser Ser Ser Pro Val Ser Thr Cys Ser Glu<br>                35                       40                  45 | 135 |
| TCA GTG AGA GCC AAG GCT GCC AAG TCT GAC TGG CTG CGA GAT CTT<br>Ser Val Arg Ala Lys Ala Ala Lys Ser Asp Trp Leu Arg Asp Leu<br>                50                       55                  60 | 180 |
| TTC CTG CCG AAC ATC ACA CTC TTC ATA GAC AAG AGT TAC TTC AAT<br>Phe Leu Pro Asn Ile Thr Leu Phe Ile Asp Lys Ser Tyr Phe Asn<br>                65                       70                  75 | 225 |
| GTC AGT GAG TGG GAC CGC CTG GAG CAT TTT GCA CCT CCC TAT GGC<br>Val Ser Glu Trp Asp Arg Leu Glu His Phe Ala Pro Pro Tyr Gly<br>                80                       85                  90 | 270 |
| TTC ATG GAG CTG AAT TAC TCA CTG GTA GAA GAA GTC ATG TCA CGG<br>Phe MET Glu Leu Asn Tyr Ser Leu Val Glu Glu Val MET Ser Arg<br>                95                      100                105 | 315 |
| CTG CCT CCA AAT CCC CAC CAG CAG CTG CTC CTG GCC AAC AGT AGC<br>Leu Pro Pro Asn Pro His Gln Gln Leu Leu Leu Ala Asn Ser Ser<br>                110                     115               120 | 360 |
| AGC AAC GTG TCA ACG TGC ATC AGC TGT GCT GTT GTG GGG AAT GGA<br>Ser Asn Val Ser Thr Cys Ile Ser Cys Ala Val Val Gly Asn Gly<br>                125                     130               135 | 405 |
| GGG ATA TTG AAT AAC TCT GGA ATG GGC CAG GAG ATT GAC TCC CAT<br>Gly Ile Leu Asn Asn Ser Gly MET Gly Gln Glu Ile Asp Ser His<br>                140                     145               150 | 450 |

```
GAC TAT GTG TTC CGG GTG AGC GGG GCT GTA ATC AAA GGT TAC GAA          495
Asp Tyr Val Phe Arg Val Ser Gly Ala Val Ile Lys Gly Tyr Glu
            155                 160                 165

AAG GAT GTG GGA ACA AAA ACC TCC TTC TAC GGA TTC ACA GCG TAC          540
Lys Asp Val Gly Thr Lys Thr Ser Phe Tyr Gly Phe Thr Ala Tyr
            170                 175                 180

TCC CTG GTG TCC TCT CTC CAG AAC TTG GGA CAC AAA GGG TTC AAG          585
Ser Leu Val Ser Ser Leu Gln Asn Leu Gly His Lys Gly Phe Lys
            185                 190                 195

AAG ATC CCA CAG GGG AAG CAT ATC AGA TAC ATT CAC TTC CTG GAG          630
Lys Ile Pro Gln Gly Lys His Ile Arg Tyr Ile His Phe Leu Glu
            200                 205                 210

GCA GTT AGA GAC TAT GAG TGG CTG AAG GCT CTT CTG TTG GAC AAG          675
Ala Val Arg Asp Tyr Glu Trp Leu Lys Ala Leu Leu Leu Asp Lys
            215                 220                 225

GAT ATC AGG AAA GGA TTC CTG AAC TAC TAT GGG CGA AGG CCC CGG          720
Asp Ile Arg Lys Gly Phe Leu Asn Tyr Tyr Gly Arg Arg Pro Arg
            230                 235                 240

GAG AGA TTC GAT GAA GAT TTC ACA ATG AAT AAG TAC CTG GTA GCT          765
Glu Arg Phe Asp Glu Asp Phe Thr MET Asn Lys Tyr Leu Val Ala
            245                 250                 255

CAC CCT GAT TTC CTC AGA TAC TTG AAA AAC AGG TTC TTA AAA TCT          810
His Pro Asp Phe Leu Arg Tyr Leu Lys Asn Arg Phe Leu Lys Ser
            260                 265                 270

AAA AAT CTG CAA AAG CCC TAC TGG CGG CTG TAC AGA CCC ACA ACA          855
Lys Asn Leu Gln Lys Pro Tyr Trp Arg Leu Tyr Arg Pro Thr Thr
            275                 280                 285

GGA GCC CTC CTG CTG CTG ACT GCC CTG CAT CTC TGT GAC CGG GTG          900
Gly Ala Leu Leu Leu Leu Thr Ala Leu His Leu Cys Asp Arg Val
            290                 295                 300

AGT GCC TAT GGC TAC ATC ACA GAA GGT CAC CAG AAG TAC TCG GAT          945
Ser Ala Tyr Gly Tyr Ile Thr Glu Gly His Gln Lys Tyr Ser Asp
            305                 310                 315

CAC TAC TAT GAC AAG GAG TGG AAA CGC CTG GTC TTC TAC GTT AAC          990
His Tyr Tyr Asp Lys Glu Trp Lys Arg Leu Val Phe Tyr Val Asn
            320                 325                 330

CAT GAC TTC AAC TTG GAG AAG CAG GTG TGG AAA AGG CTT CAT GAT         1035
His Asp Phe Asn Leu Glu Lys Gln Val Trp Lys Arg Leu His Asp
            335                 340                 345

GAG AAC ATC ATG AAG CTC TAC CAG AGA TCC TGA CAGTGTGCCGA G           1080
Glu Asn Ile MET Lys Leu Tyr Gln Arg Ser
            350                 355

GGCCATTGCC TGGGAAATCT CAACAGCACC TCATGGGGAA CAGAAGAGGA              1130

CCTCGGAAGC CAGGGTTAGC TCTGGACTTC CAGGCCCAGC TTCAGCTCCA              1180

CAGAGATATT TCCCTCCTTT GATATC                                        1206

(2) INFORMATION FOR SEQ ID NO:3:

(i) SEQUENCE CHARACTERISTICS:
        (A) LENGTH: 1666
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: G. gallus (chicken)

(ix) FEATURE:
        (D) OTHER INFORMATION: CDS  1-1212
```

-continued (xi) SEQUENCE DESCRIPTION: SEQ ID NO:3:

```
ATG GGT TCC CCC CGC TGG AAG CGT TTC TGC TTC TTG CTC CTC GCA       45
MET Gly Ser Pro Arg Trp Lys Arg Phe Cys Phe Leu Leu Leu Ala
1               5                  10                  15

GCC TTC ACC TCG TCC CTT CTG CTC TAC GGG CAC TAC TAC GCT ACG       90
Ala Phe Thr Ser Ser Leu Leu Leu Tyr Gly His Tyr Tyr Ala Thr
                20                  25                  30

GTG GAC GTG CGC AGC GGC CCG AGG GTC GTG ACC AGC CTG CTG CAG      135
Val Asp Val Arg Ser Gly Pro Arg Val Val Thr Ser Leu Leu Gln
                35                  40                  45

CCA GAG CTG CTG TTC CTG GTC CGC CCA GAC ACC CCA CAC CCA GAC      180
Pro Glu Leu Leu Phe Leu Val Arg Pro Asp Thr Pro His Pro Asp
                50                  55                  60

AAC AGC CAC CAC AAG GAG CTC AGA GGG ACT GTG AAG AGC AGG GAG      225
Asn Ser His His Lys Glu Leu Arg Gly Thr Val Lys Ser Arg Glu
                65                  70                  75

TTC TTC TCC CAA CCA TCC TCA GAG CTG GAG AAG CCC AAA CCC AGT      270
Phe Phe Ser Gln Pro Ser Ser Glu Leu Glu Lys Pro Lys Pro Ser
                80                  85                  90

GGA AAG CAG CCC ACC CCG TGC CCC CGC TCG GTG GCA GCC ACG GCG      315
Gly Lys Gln Pro Thr Pro Cys Pro Arg Ser Val Ala Ala Thr Ala
                95                  100                 105

AAG GCA GAC CCC ACG TTT GGG GAG CTC TTC CAA TTT GAC ATC CCG      360
Lys Ala Asp Pro Thr Phe Gly Glu Leu Phe Gln Phe Asp Ile Pro
                110                 115                 120

GTG CTG ATG TGG GAC CAA CAC TTC AAC CCT GAG ACG TGG GAC AGG      405
Val Leu Met Trp Asp Gln His Phe Asn Pro Glu Thr Trp Asp Arg
                125                 130                 135

CTG AAG GCA CGA CGC GTC CCA TAC GGC TGG CAG GGT TTG TCC CAA      450
Leu Lys Ala Arg Arg Val Pro Tyr Gly Trp Gln Gly Leu Ser Gln
                140                 145                 150

GCA GCT GTC GGC AGC ACC CTG CGT CTC CTT AAC ACC TCC TCC AAC      495
Ala Ala Val Gly Ser Thr Leu Arg Leu Leu Asn Thr Ser Ser Asn
                155                 160                 165

ACG CGG CTC TTC GAC CGC CAC CTC TTC CCC GGG GGC TGC ATC CGC      540
Thr Arg Leu Phe Asp Arg His Leu Phe Pro Gly Gly Cys Ile Arg
                170                 175                 180

TGT GCC GTG GTG GGC AAT GGG GGA ATC CTC AAC GGC TCA CGG CAG      585
Cys Ala Val Val Gly Asn Gly Gly Ile Leu Asn Gly Ser Arg Gln
                185                 190                 195

GGC CGG GCC ATC GAC GCA CAT GAT TTG GTC TTC AGG CTG AAC GGG      630
Gly Arg Ala Ile Asp Ala His Asp Leu Val Phe Arg Leu Asn Gly
                200                 205                 210

GCC ATC ACC AAA GGC TTT GAG GAG GAT GTT GGG AGC AAG GTT TCG      675
Ala Ile Thr Lys Gly Phe Glu Glu Asp Val Gly Ser Lys Val Ser
                215                 220                 225

TTC TAC GGC TTC ACG GTG AAC ACC ATG AAG AAC TCA CTC ATT GCC      720
Phe Tyr Gly Phe Thr Val Asn Thr Met Lys Asn Ser Leu Ile Ala
                230                 235                 240

TAT GAG GCG TAT GGC TTC ACC CGG ACA CCG CAG GGC AAG GAC CTG      765
Tyr Glu Ala Tyr Gly Phe Thr Arg Thr Pro Gln Gly Lys Asp Leu
                245                 250                 255

AAG TAC ATC TTC ATC CCC TCG GAC GCA CGC GAC TAC ATC ATG CTG      810
Lys Tyr Ile Phe Ile Pro Ser Asp Ala Arg Asp Tyr Ile Met Leu
                260                 265                 270

AGG TCG GCC ATT CAG GGC AGC CCA GTC CCC GAG GGC TTG GAC AAG      855
Arg Ser Ala Ile Gln Gly Ser Pro Val Pro Glu Gly Leu Asp Lys
                275                 280                 285

GGC GAC GAG CCA CAG AAG TAT TTT GGA CTG GAG GCA TCT GCG GAG      900
```

```
                                     -continued

Gly Asp Glu Pro Gln Lys Tyr Phe Gly Leu Glu Ala Ser Ala Glu
            290                 295                 300

AAG TTC AAG CTG CTG CAT CCC GAT TTC TTG CAT TAC CTG ACA ACC        945
Lys Phe Lys Leu Leu His Pro Asp Phe Leu His Tyr Leu Thr Thr
            305                 310                 315

AGG TTC CTG AGG TCA GAG CTC CTG GAC ATG CAG TAC GGC CAC CTC        990
Arg Phe Leu Arg Ser Glu Leu Leu Asp Met Gln Tyr Gly His Leu
            320                 325                 330

TAC ATG CCC AGC ACT GGG GCA CTC ATG CTG CTG ACA GCA CTG CAC       1035
Tyr Met Pro Ser Thr Gly Ala Leu Met Leu Leu Thr Ala Leu His
            335                 340                 345

ACC TGC GAC CAG GTC AGT GCC TAC GGG TTC ATC ACA GCC AAC TAC       1080
Thr Cys Asp Gln Val Ser Ala Tyr Gly Phe Ile Thr Ala Asn Tyr
            350                 355                 360

GAG CAG TTC TCC GAC CAT TAC TAC GAG CCA GAG AAG AAG CCA CTG       1125
Glu Gln Phe Ser Asp His Tyr Tyr Glu Pro Glu Lys Lys Pro Leu
            365                 370                 375

GTG TTC TAC GCC AAC CAC GAC ATG CTG CTG GAA GCA GAG CTG TGG       1170
Val Phe Tyr Ala Asn His Asp Met Leu Leu Glu Ala Glu Leu Trp
            380                 385                 390

AGG AGT TTG CAC CGG GCG GGG ATC ATG GAG CTG TAC CAG CGG TGA       1215
Arg Ser Leu His Arg Ala Gly Ile Met Glu Leu Tyr Gln Arg
            395                 400

GGGCAGCGCA GTCCCACTGC AAGGACTCTC AATGCAACGC AGAAGCGGTT CTCCTCTTTC    1275

CTGAAGGCCT CCTTCTGTCC CTGGAGGGCT CTCCCACACT GGCGGGCCAG CCTGAGGAGC    1335

AGGGCCTGCA GCTGACAGCA GAGCAAAGGT GGTGGTGCAG GGCGAGCCAA GGCTGGCAGG    1395

GAAATACTGC AACTCCTCAG GGCCCTTCAG CATCTTATTT GTGACTCTGA GACTGAGCAC    1455

GGCCTTGGGG AGCCTCCGCA CGTGGCTGTG AGCTCCTGAT GCCATGAGAA TGTCTGTGGG    1515

GTGGCAGCAG CCCCTGGGAA GCACAGTGTT CATGTGCAGG TGGGGCACAG TGGTGCTGGA    1575

AGGGGATGCT GGAGAAGCAT ACATCTGACA GACCTCACTT CTTGGAACTT CCTGGAGTTG    1635

CAGCCTCGAA GTCACGCTGG GTAGGCTGCA G                                   1666

(2) INFORMATION FOR SEQ ID NO:4:

(i) SEQUENCE CHARACTERISTICS:
        (A) LENGTH: 1146
        (B) TYPE: nucleic acid
        (C) STRANDEDNESS: double
        (D) TOPOLOGY: linear (ii) MOLECULE TYPE: DNA (vi) ORIGINAL SOURCE:
        (A) ORGANISM: mouse (ix) FEATURE:
        (D) OTHER INFORMATION: 1-1128 sialyltransferase in soluble
            form (xi) SEQUENCE DESCRIPTION: SEQ ID NO:4:

ATG GGG AGC GAC TAT GAG GCT CTT ACA TTG CAA GCC AAG GTA TTC         45
MET Gly Ser Asp Tyr Glu Ala Leu Thr Leu Gln Ala Lys Val Phe
 1               5                  10                  15

CAG ATG CCG AAG AGC CAG GAG AAA GTG GCC GTG GGG CCT GCT CCC         90
Gln MET Pro Lys Ser Gln Glu Lys Val Ala Val Gly Pro Ala Pro
            20                  25                  30

CAG GCT GTG TTC TCA AAC AGC AAA CAA GAC CCT AAG GAA GGC GTT        135
Gln Ala Val Phe Ser Asn Ser Lys Gln Asp Pro Lys Glu Gly Val
            35                  40                  45
```

```
CAG ATC CTC AGT TAC CCC AGG GTC ACA GCC AAG GTC AAG CCA CAG        180
Gln Ile Leu Ser Tyr Pro Arg Val Thr Ala Lys Val Lys Pro Gln
                50                  55                  60

CCC TCC TTG CAG GTG TGG GAC AAG GAC TCC ACA TAC TCA AAA CTT        225
Pro Ser Leu Gln Val Trp Asp Lys Asp Ser Thr Tyr Ser Lys Leu
            65                  70                  75

AAC CCC AGG CTG CTG AAG ATC TGG AGG AAC TAT CTG AAC ATG AAT        270
Asn Pro Arg Leu Leu Lys Ile Trp Arg Asn Tyr Leu Asn MET Asn
                80                  85                  90

AAA TAT AAA GTG TCC TAC AAG GGG CCG GGA CCA GGA GTC AGG TTC        315
Lys Tyr Lys Val Ser Tyr Lys Gly Pro Gly Pro Gly Val Arg Phe
                95                  100                 105

AGC GTA GAA GGC CTG CGC TGC CAC CTT CGA GAC CAC GTG AAT GTG        360
Ser Val Glu Gly Leu Arg Cys His Leu Arg Asp His Val Asn Val
            110                 115                 120

TCT ATG ATA GAG GCC ACA GAT TCT CCC TTC AAC ACC ACT GAA TGG        405
Ser MET Ile Glu Ala Thr Asp Ser Pro Phe Asn Thr Thr Glu Trp
                125                 130                 135

GAG GGT TAC CTG CCC AAA GAG ACA TTC AGA ACC AAG GCT GGG CCT        450
Glu Gly Tyr Leu Pro Lys Glu Thr Phe Arg Thr Lys Ala Gly Pro
            140                 145                 150

TGC ACA AAG TGT GCC GTC GTG TCT TCT GCA GGA TCT CTG AAG AAC        495
Cys Thr Lys Cys Ala Val Val Ser Ser Ala Gly Ser Leu Lys Asn
                155                 160                 165

TCC CAG CTG GGT CGA GAG ATT GAT AAT CAT GAT GCG GTC CTG AGG        540
Ser Gln Leu Gly Arg Glu Ile Asp Asn His Asp Ala Val Leu Arg
            170                 175                 180

TTT AAT GGG GCA CCT ACA GAC AAC TTC CAA CAG GAT GTG GGC ACA        585
Phe Asn Gly Ala Pro Thr Asp Asn Phe Gln Gln Asp Val Gly Thr
                185                 190                 195

AAA ACT ACC ATC CGC CTA GTG AAC TCT CAG TTA GTC ACC ACA GAA        630
Lys Thr Thr Ile Arg Leu Val Asn Ser Gln Leu Val Thr Thr Glu
            200                 205                 210

AAG CGC TTC CTG AAG GAC AGT TTG TAC ACC GAA GGA ATC CTG ATT        675
Lys Arg Phe Leu Lys Asp Ser Leu Tyr Thr Glu Gly Ile Leu Ile
                215                 220                 225

CTG TGG GAC CCA TCT GTG TAT CAT GCA GAC ATT CCG CAG TGG TAT        720
Leu Trp Asp Pro Ser Val Tyr His Ala Asp Ile Pro Gln Trp Tyr
            230                 235                 240

CAG AAG CCA GAC TAC AAC TTC TTC GAA ACC TAT AAG AGT TAC CGA        765
Gln Lys Pro Asp Tyr Asn Phe Phe Glu Thr Tyr Lys Ser Tyr Arg
                245                 250                 255

AGG CTT CAC CCC AGC CAG CCT TTT TAC ATC CTC AAG CCC CAG ATG        810
Arg Leu His Pro Ser Gln Pro Phe Tyr Ile Leu Lys Pro Gln MET
            260                 265                 270

CCA TGG GAA CTA TGG GAC ATC ATT CAG GAA ATC TCT CCA GAT CTG        855
Pro Trp Glu Leu Trp Asp Ile Ile Gln Glu Ile Ser Pro Asp Leu
                275                 280                 285

ATT CAG CCG AAT CCC CCA TCC TCC GGC ATG CTG GGT ATC ATC ATT        900
Ile Gln Pro Asn Pro Pro Ser Ser Gly MET Leu Gly Ile Ile Ile
            290                 295                 300

ATG ATG ACG CTG TGT GAC CAA GTT GAT ATT TAC GAG TTC CTC CCA        945
MET MET Thr Leu Cys Asp Gln Val Asp Ile Tyr Glu Phe Leu Pro
                305                 310                 315

TCC AAG CGC AAG ACA GAT GTG TGC TAC TAT CAC CAG AAG TTC TTT        990
Ser Lys Arg Lys Thr Asp Val Cys Tyr Tyr His Gln Lys Phe Phe
            320                 325                 330

GAC AGC GCC TGC ACG ATG GGT GCC TAC CAT CCG CTC CTC TTC GAG       1035
Asp Ser Ala Cys Thr MET Gly Ala Tyr His Pro Leu Leu Phe Glu
                335                 340                 345
```

```
AAG AAT ATG GTG AAG CAT CTC AAT GAG GGA ACA GAT GAA GAC ATT   1080
Lys Asn MET Val Lys His Leu Asn Glu Gly Thr Asp Glu Asp Ile
            350                 355                 360

TAT TTG TTT GGG AAA GCT ACC CTG TCT GGC TTC CGG AAC AAT CGC   1125
Tyr Leu Phe Gly Lys Ala Thr Leu Ser Gly Phe Arg Asn Asn Arg
            365                 370                 375

TGT TGA GCCAGGGATC CTCAT                                      1146
Cys
```

(2) INFORMATION FOR SEQ ID NO:5:

(i) SEQUENCE CHARACTERISTICS:
        (A) LENGTH: 566 amino acids
        (B) TYPE: amino acid
        (C) STRANDEDNESS: single
        (D) TOPOLOGY: linear (xi) SEQUENCE DESCRIPTION: SEQ ID NO:5:

```
MET Gly Phe Leu Ile Arg Arg Leu Pro Lys Asp Ser Arg Ile Phe
 1               5                  10                  15

Arg Trp Leu Leu Ile Leu Thr Val Phe Ser Phe Ile Ile Thr Ser
                20                  25                  30

Phe Ser Ala Leu Phe Gly MET Glu Lys Ser Ile Phe Arg Gln Leu
                35                  40                  45

Lys Ile Tyr Gln Ser Ile Ala His MET Leu Gln Val Asp Thr Gln
                50                  55                  60

Asp Gln Gln Gly Ser Asn Tyr Ser Ala Asn Gly Arg Ile Ser Lys
                65                  70                  75

Val Gly Leu Glu Arg Asp Ile Ala Trp Leu Glu Leu Asn Thr Ala
                80                  85                  90

Val Ser Thr Pro Ser Gly Glu Gly Lys Glu Glu Gln Lys Lys Thr
                95                 100                 105

Val Lys Pro Val Ala Lys Val Glu Glu Ala Lys Glu Lys Val Thr
               110                 115                 120

Val Lys Pro Phe Pro Glu Val MET Gly Ile Thr Asn Thr Thr Ala
               125                 130                 135

Ser Thr Ala Ser Val Val Glu Arg Thr Lys Glu Lys Thr Thr Ala
               140                 145                 150

Arg Pro Val Pro Gly Val Gly Glu Ala Asp Gly Lys Arg Thr Thr
               155                 160                 165

Ile Ala Leu Pro Ser MET Lys Glu Asp Lys Glu Lys Ala Thr Val
               170                 175                 180

Lys Pro Ser Phe Gly MET Lys Val Ala His Ala Asn Ser Thr Ser
               185                 190                 195

Lys Asp Lys Pro Lys Ala Glu Glu Pro Pro Ala Ser Val Lys Ala
               200                 205                 210

Ile Arg Pro Val Thr Gln Ala Ala Thr Val Thr Glu Lys Lys Lys
               215                 220                 225

Leu Arg Ala Ala Asp Phe Lys Thr Glu Pro Gln Trp Asp Phe Asp
               230                 235                 240

Asp Glu Tyr Ile Leu Asp Ser Ser Ser Pro Val Ser Thr Cys Ser
               245                 250                 255

Glu Ser Val Arg Ala Lys Ala Ala Lys Ser Asp Trp Leu Arg Asp
               260                 265                 270

Leu Phe Leu Pro Asn Ile Thr Leu Phe Ile Asp Lys Ser Tyr Phe
               275                 280                 285
```

Asn Val Ser Glu Trp Asp Arg Leu Glu His Phe Ala Pro Pro Tyr
            290                 295                 300

Gly Phe MET Glu Leu Asn Tyr Ser Leu Val Glu Glu Val MET Ser
            305                 310                 315

Arg Leu Pro Pro Asn Pro His Gln Gln Leu Leu Leu Ala Asn Ser
            320                 325                 330

Ser Ser Asn Val Ser Thr Cys Ile Ser Cys Ala Val Val Gly Asn
            335                 340                 345

Gly Gly Ile Leu Asn Asn Ser Gly MET Gly Gln Glu Ile Asp Ser
            350                 355                 360

His Asp Tyr Val Phe Arg Val Ser Gly Ala Val Ile Lys Gly Tyr
            365                 370                 375

Glu Lys Asp Val Gly Thr Lys Thr Ser Phe Tyr Gly Phe Thr Ala
            380                 385                 390

Tyr Ser Leu Val Ser Ser Leu Gln Asn Leu Gly His Lys Gly Phe
            395                 400                 405

Lys Lys Ile Pro Gln Gly Lys His Ile Arg Tyr Ile His Phe Leu
            410                 415                 420

Glu Ala Val Arg Asp Tyr Glu Trp Leu Lys Ala Leu Leu Leu Asp
            425                 430                 435

Lys Asp Ile Arg Lys Gly Phe Leu Asn Tyr Tyr Gly Arg Arg Pro
            440                 445                 450

Arg Glu Arg Phe Asp Glu Asp Phe Thr MET Asn Lys Tyr Leu Val
            455                 460                 465

Ala His Pro Asp Phe Leu Arg Tyr Leu Lys Asn Arg Phe Leu Lys
            470                 475                 480

Ser Lys Asn Leu Gln Lys Pro Tyr Trp Arg Leu Tyr Arg Pro Thr
            485                 490                 495

Thr Gly Ala Leu Leu Leu Thr Ala Leu His Leu Cys Asp Arg
            500                 505                 510

Val Ser Ala Tyr Gly Tyr Ile Thr Glu Gly His Gln Lys Tyr Ser
            515                 520                 525

Asp His Tyr Tyr Asp Lys Glu Trp Lys Arg Leu Val Phe Tyr Val
            530                 535                 540

Asn His Asp Phe Asn Leu Glu Lys Gln Val Trp Lys Arg Leu His
            545                 550                 555

Asp Glu Asn Ile MET Lys Leu Tyr Gln Arg Ser
            560                 565

(2) INFORMATION FOR SEQ ID NO:6:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO:6:

MET Lys Phe Ser Trp Val MET Phe Phe Leu MET Ala Val Val Thr
 1              5                  10                  15

Gly Val Asn Ser Glu Phe Thr Glu Pro Gln Trp Asp Phe Asp Asp
            20                  25                  30

Glu Tyr Ile Leu Asp Ser Ser Pro Val Ser Thr Cys Ser Glu
            35                  40                  45

Ser Val Arg Ala Lys Ala Ala Lys Ser Asp Trp Leu Arg Asp Leu

-continued

```
                50                    55                    60
Phe Leu Pro Asn Ile Thr Leu Phe Ile Asp Lys Ser Tyr Phe Asn
                    65                    70                    75
Val Ser Glu Trp Asp Arg Leu Glu His Phe Ala Pro Tyr Gly
                    80                    85                    90
Phe MET Glu Leu Asn Tyr Ser Leu Val Glu Glu Val MET Ser Arg
                    95                   100                   105
Leu Pro Pro Asn Pro His Gln Gln Leu Leu Leu Ala Asn Ser Ser
                   110                   115                   120
Ser Asn Val Ser Thr Cys Ile Ser Cys Ala Val Val Gly Asn Gly
                   125                   130                   135
Gly Ile Leu Asn Asn Ser Gly MET Gly Gln Glu Ile Asp Ser His
                   140                   145                   150
Asp Tyr Val Phe Arg Val Ser Gly Ala Val Ile Lys Gly Tyr Glu
                   155                   160                   165
Lys Asp Val Gly Thr Lys Thr Ser Phe Tyr Gly Phe Thr Ala Tyr
                   170                   175                   180
Ser Leu Val Ser Ser Leu Gln Asn Leu Gly His Lys Gly Phe Lys
                   185                   190                   195
Lys Ile Pro Gln Gly Lys His Ile Arg Tyr Ile His Phe Leu Glu
                   200                   205                   210
Ala Val Arg Asp Tyr Glu Trp Leu Lys Ala Leu Leu Leu Asp Lys
                   215                   220                   225
Asp Ile Arg Lys Gly Phe Leu Asn Tyr Tyr Gly Arg Arg Pro Arg
                   230                   235                   240
Glu Arg Phe Asp Glu Asp Phe Thr MET Asn Lys Tyr Leu Val Ala
                   245                   250                   255
His Pro Asp Phe Leu Arg Tyr Leu Lys Asn Arg Phe Leu Lys Ser
                   260                   265                   270
Lys Asn Leu Gln Lys Pro Tyr Trp Arg Leu Tyr Arg Pro Thr Thr
                   275                   280                   285
Gly Ala Leu Leu Leu Leu Thr Ala Leu His Leu Cys Asp Arg Val
                   290                   295                   300
Ser Ala Tyr Gly Tyr Ile Thr Glu Gly His Gln Lys Tyr Ser Asp
                   305                   310                   315
His Tyr Tyr Asp Lys Glu Trp Lys Arg Leu Val Phe Tyr Val Asn
                   320                   325                   330
His Asp Phe Asn Leu Glu Lys Gln Val Trp Lys Arg Leu His Asp
                   335                   340                   345
Glu Asn Ile MET Lys Leu Tyr Gln Arg Ser
                   350                   355
```

(2) INFORMATION FOR SEQ ID NO:7:

(i) SEQUENCE CHARACTERISTICS:
        (A) LENGTH: 404 amino acids
        (B) TYPE: amino acid
        (C) STRANDEDNESS: single
        (D) TOPOLOGY: linear (vi) ORIGINAL SOURCE:
        (A) ORGANISM: G. gallus (chicken)

(xi) SEQUENCE DESCRIPTION: SEQ ID NO:7:

```
MET Gly Ser Pro Arg Trp Lys Arg Phe Cys Phe Leu Leu Leu Ala
  1                 5                    10                    15
```

-continued

```
Ala Phe Thr Ser Ser Leu Leu Tyr Gly His Tyr Ala Thr
                 20                  25                  30

Val Asp Val Arg Ser Gly Pro Arg Val Thr Ser Leu Leu Gln
                 35                  40                  45

Pro Glu Leu Leu Phe Leu Val Arg Pro Asp Thr Pro His Pro Asp
                 50                  55                  60

Asn Ser His His Lys Glu Leu Arg Gly Thr Val Lys Ser Arg Glu
                 65                  70                  75

Phe Phe Ser Gln Pro Ser Ser Glu Leu Glu Lys Pro Lys Pro Ser
                 80                  85                  90

Gly Lys Gln Pro Thr Pro Cys Pro Arg Ser Val Ala Ala Thr Ala
                 95                 100                 105

Lys Ala Asp Pro Thr Phe Gly Glu Leu Phe Gln Phe Asp Ile Pro
                110                 115                 120

Val Leu Met Trp Asp Gln His Phe Asn Pro Glu Thr Trp Asp Arg
                125                 130                 135

Leu Lys Ala Arg Arg Val Pro Tyr Gly Trp Gln Gly Leu Ser Gln
                140                 145                 150

Ala Ala Val Gly Ser Thr Leu Arg Leu Leu Asn Thr Ser Ser Asn
                155                 160                 165

Thr Arg Leu Phe Asp Arg His Leu Phe Pro Gly Gly Cys Ile Arg
                170                 175                 180

Cys Ala Val Val Gly Asn Gly Gly Ile Leu Asn Gly Ser Arg Gln
                185                 190                 195

Gly Arg Ala Ile Asp Ala His Asp Leu Val Phe Arg Leu Asn Gly
                200                 205                 210

Ala Ile Thr Lys Gly Phe Glu Glu Asp Val Gly Ser Lys Val Ser
                215                 220                 225

Phe Tyr Gly Phe Thr Val Asn Thr Met Lys Asn Ser Leu Ile Ala
                230                 235                 240

Tyr Glu Ala Tyr Gly Phe Thr Arg Thr Pro Gln Gly Lys Asp Leu
                245                 250                 255

Lys Tyr Ile Phe Ile Pro Ser Asp Ala Arg Asp Tyr Ile Met Leu
                260                 265                 270

Arg Ser Ala Ile Gln Gly Ser Pro Val Pro Glu Gly Leu Asp Lys
                275                 280                 285

Gly Asp Glu Pro Gln Lys Tyr Phe Gly Leu Glu Ala Ser Ala Glu
                290                 295                 300

Lys Phe Lys Leu Leu His Pro Asp Phe Leu His Tyr Leu Thr Thr
                305                 310                 315

Arg Phe Leu Arg Ser Glu Leu Leu Asp Met Gln Tyr Gly His Leu
                320                 325                 330

Tyr Met Pro Ser Thr Gly Ala Leu Met Leu Leu Thr Ala Leu His
                335                 340                 345

Thr Cys Asp Gln Val Ser Ala Tyr Gly Phe Ile Thr Ala Asn Tyr
                350                 355                 360

Glu Gln Phe Ser Asp His Tyr Tyr Glu Pro Glu Lys Lys Pro Leu
                365                 370                 375

Val Phe Tyr Ala Asn His Asp Met Leu Leu Glu Ala Glu Leu Trp
                380                 385                 390

Arg Ser Leu His Arg Ala Gly Ile Met Glu Leu Tyr Gln Arg
                395                 400
```

-continued (2) INFORMATION FOR SEQ ID NO:8:

(i) SEQUENCE CHARACTERISTICS:
        (A) LENGTH: 376 amino acids
        (B) TYPE: amino acid
        (C) STRANDEDNESS: single
        (D) TOPOLOGY: linear (vi) ORIGINAL SOURCE:
        (A) ORGANISM: mouse (xi) SEQUENCE DESCRIPTION: SEQ ID NO:8:

```
MET Gly Ser Asp Tyr Glu Ala Leu Thr Leu Gln Ala Lys Val Phe
 1               5                  10                  15

Gln MET Pro Lys Ser Gln Glu Lys Val Ala Val Gly Pro Ala Pro
                20                  25                  30

Gln Ala Val Phe Ser Asn Ser Lys Gln Asp Pro Lys Glu Gly Val
                35                  40                  45

Gln Ile Leu Ser Tyr Pro Arg Val Thr Ala Lys Val Lys Pro Gln
                50                  55                  60

Pro Ser Leu Gln Val Trp Asp Lys Asp Ser Thr Tyr Ser Lys Leu
                65                  70                  75

Asn Pro Arg Leu Leu Lys Ile Trp Arg Asn Tyr Leu Asn MET Asn
                80                  85                  90

Lys Tyr Lys Val Ser Tyr Lys Gly Pro Gly Pro Val Arg Phe
                95                  100                 105

Ser Val Glu Gly Leu Arg Cys His Leu Arg Asp His Val Asn Val
                110                 115                 120

Ser MET Ile Glu Ala Thr Asp Ser Pro Phe Asn Thr Thr Glu Trp
                125                 130                 135

Glu Gly Tyr Leu Pro Lys Glu Thr Phe Arg Thr Lys Ala Gly Pro
                140                 145                 150

Cys Thr Lys Cys Ala Val Val Ser Ser Ala Gly Ser Leu Lys Asn
                155                 160                 165

Ser Gln Leu Gly Arg Glu Ile Asp Asn His Asp Ala Val Leu Arg
                170                 175                 180

Phe Asn Gly Ala Pro Thr Asp Asn Phe Gln Gln Asp Val Gly Thr
                185                 190                 195

Lys Thr Thr Ile Arg Leu Val Asn Ser Gln Leu Val Thr Thr Glu
                200                 205                 210

Lys Arg Phe Leu Lys Asp Ser Leu Tyr Thr Glu Gly Ile Leu Ile
                215                 220                 225

Leu Trp Asp Pro Ser Val Tyr His Ala Asp Ile Pro Gln Trp Tyr
                230                 235                 240

Gln Lys Pro Asp Tyr Asn Phe Phe Glu Thr Tyr Lys Ser Tyr Arg
                245                 250                 255

Arg Leu His Pro Ser Gln Pro Phe Tyr Ile Leu Lys Pro Gln MET
                260                 265                 270

Pro Trp Glu Leu Trp Asp Ile Ile Gln Glu Ile Ser Pro Asp Leu
                275                 280                 285

Ile Gln Pro Asn Pro Pro Ser Ser Gly MET Leu Gly Ile Ile Ile
                290                 295                 300

MET MET Thr Leu Cys Asp Gln Val Asp Ile Tyr Glu Phe Leu Pro
                305                 310                 315

Ser Lys Arg Lys Thr Asp Val Cys Tyr Tyr His Gln Lys Phe Phe
                320                 325                 330
```

-continued

```
Asp Ser Ala Cys Thr MET Gly Ala Tyr His Pro Leu Leu Phe Glu
                335                 340                 345

Lys Asn MET Val Lys His Leu Asn Glu Gly Thr Asp Glu Asp Ile
                350                 355                 360

Tyr Leu Phe Gly Lys Ala Thr Leu Ser Gly Phe Arg Asn Asn Arg
                365                 370                 375

Cys
```